(12) United States Patent
Kim et al.

(10) Patent No.: US 11,236,304 B2
(45) Date of Patent: Feb. 1, 2022

(54) METHOD FOR DIFFERENTIATING INDUCED PLURIPOTENT STEM CELLS, WHICH ARE PREPARED FROM ENDOCARDIUM-DERIVED ADULT STEM CELLS, INTO CARDIOVASCULAR CELLS, AND USE THEREOF

(71) Applicant: SEOUL NATIONAL UNIVERSITY HOSPITAL, Seoul (KR)

(72) Inventors: Hyo-Soo Kim, Seoul (KR); Han-Mo Yang, Seoul (KR); Ju-Young Kim, Suwon-si (KR); Joo-Eun Lee, Seoul (KR)

(73) Assignee: SEOUL NATIONAL UNIVERSITY HOSPITAL, Seoul (KR)

( * ) Notice: Subject to any disclaimer, the term of this patent is extended or adjusted under 35 U.S.C. 154(b) by 855 days.

(21) Appl. No.: 15/763,289

(22) PCT Filed: Nov. 18, 2015

(86) PCT No.: PCT/KR2015/012392
§ 371 (c)(1),
(2) Date: Sep. 6, 2018

(87) PCT Pub. No.: WO2017/051978
PCT Pub. Date: Mar. 30, 2017

(65) Prior Publication Data
US 2018/0362929 A1    Dec. 20, 2018

(30) Foreign Application Priority Data
Sep. 24, 2015   (KR) .................... 10-2015-0135715

(51) Int. Cl.
C12N 5/00       (2006.01)
C12N 5/077      (2010.01)
A61K 35/34      (2015.01)
C12N 5/074      (2010.01)

(52) U.S. Cl.
CPC ............ *C12N 5/0657* (2013.01); *A61K 35/34* (2013.01); *C12N 5/0696* (2013.01); *C12N 2501/115* (2013.01); *C12N 2501/135* (2013.01); *C12N 2501/15* (2013.01); *C12N 2501/155* (2013.01); *C12N 2501/16* (2013.01); *C12N 2501/165* (2013.01); *C12N 2506/115* (2013.01); *C12N 2506/45* (2013.01)

(58) Field of Classification Search
CPC ..................... C12N 5/0696; C12N 2506/115
See application file for complete search history.

(56) References Cited

U.S. PATENT DOCUMENTS

| | | |
|---|---|---|
| 2011/0256626 A1 | 10/2011 | Park et al. |
| 2014/0242695 A1 | 8/2014 | Wang et al. |
| 2016/0102294 A1* | 4/2016 | Kim .................... A61P 9/00 424/93.7 |

FOREIGN PATENT DOCUMENTS

| | | |
|---|---|---|
| EP | 2891712 A1 | 7/2015 |
| JP | 2009-512458 A | 3/2009 |
| JP | 2012-502653 A | 2/2012 |
| JP | 2014/516557 A | 7/2014 |
| JP | 2014-520572 A | 8/2014 |
| KR | 10-2011-0032989 A | 3/2011 |
| KR | 10-1358777 B1 | 2/2014 |
| WO | 2007/010858 A1 | 1/2007 |
| WO | 2014/015777 A1 | 1/2014 |
| WO | 2014/104364 A1 | 7/2014 |
| WO | 2014/178552 A1 | 11/2014 |
| WO | 2015/040142 A1 | 3/2015 |

OTHER PUBLICATIONS

Chang et al. Stem Cell Research 10:195-202, 2013 (Year: 2013).*
Ghasemi-Dehkordi et al. KCell Commun. Signal 9:233-246, 2015 (Year: 2015).*
Patsch et al., "Generation of vascular endothelial and smooth muscle cells from human pluriopotent stem cells", Nat Cell Biol., vol. 17, No. 8—22 pages, (Aug. 2015).
Sommer et al., "Generation of Human Induced Pluripotent Stem Cells from Peripheral Blood Using the STEMCCA Lentiviral Vector", Journal of Visualized Experiments, vol. 68—5 pages, (Oct. 31, 2012).
Batalov et al., "Differentiation of Cardiomyocytes from Human Pluripotent Stem Cells Using Monolayer Culture", Biomarker Insights, vol. 10(S1)—6 pages, (May 27, 2015).
International Search Report of PCT/KR2015/012392 which is the parent application and its English translation—6 pages, (dated Jun. 22, 2016).
Office Action of Japanese Patent Application No. 2018-515668—13 pages (dated Apr. 24, 2019).
Office Action of Japanese Patent Application No. 2018-515668—8 pages (dated Nov. 27, 2019).

* cited by examiner

*Primary Examiner* — Marcia S Noble
(74) *Attorney, Agent, or Firm* — Knobbe, Martens, Olson & Bear, LLP

(57) ABSTRACT

Disclosed are a method for preparing induced pluripotent stem cells from endocardium-derived adult stem cells isolated from peripheral blood and a method for differentiating induced pluripotent stem cells into cardiovascular cells. The endocardium-derived adult stem cells are primary culture cells for preparing induced pluripotent stem cells, can be readily isolated and cultured only with a small amount of peripheral blood, have a high proliferation property so as to be storable without generic variation, and can rapidly ensure a cell number so as to be usable in cell therapy. The endocardium-derived adult stem cells have sternness, thereby having high preparation efficiency, and are derived from the endocardium so as to have the epigenetic memory of cardiovascular cells, thereby having an advantage of being able to be differentiated, after preparing induced pluripotent stem cells, into cardiovascular cells such as endothelial cells, smooth muscle cells and cardiomyocytes with a high efficiency.

3 Claims, 22 Drawing Sheets

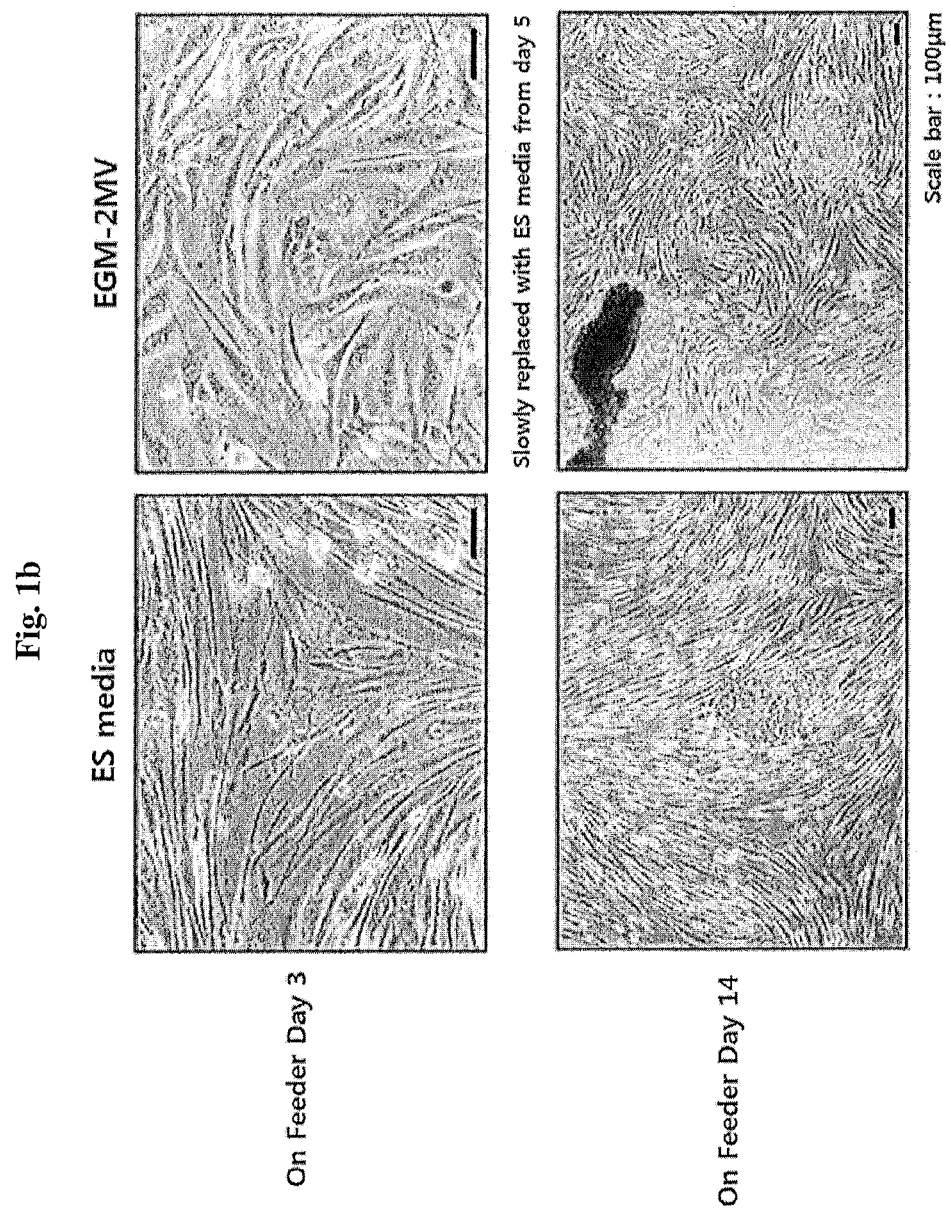

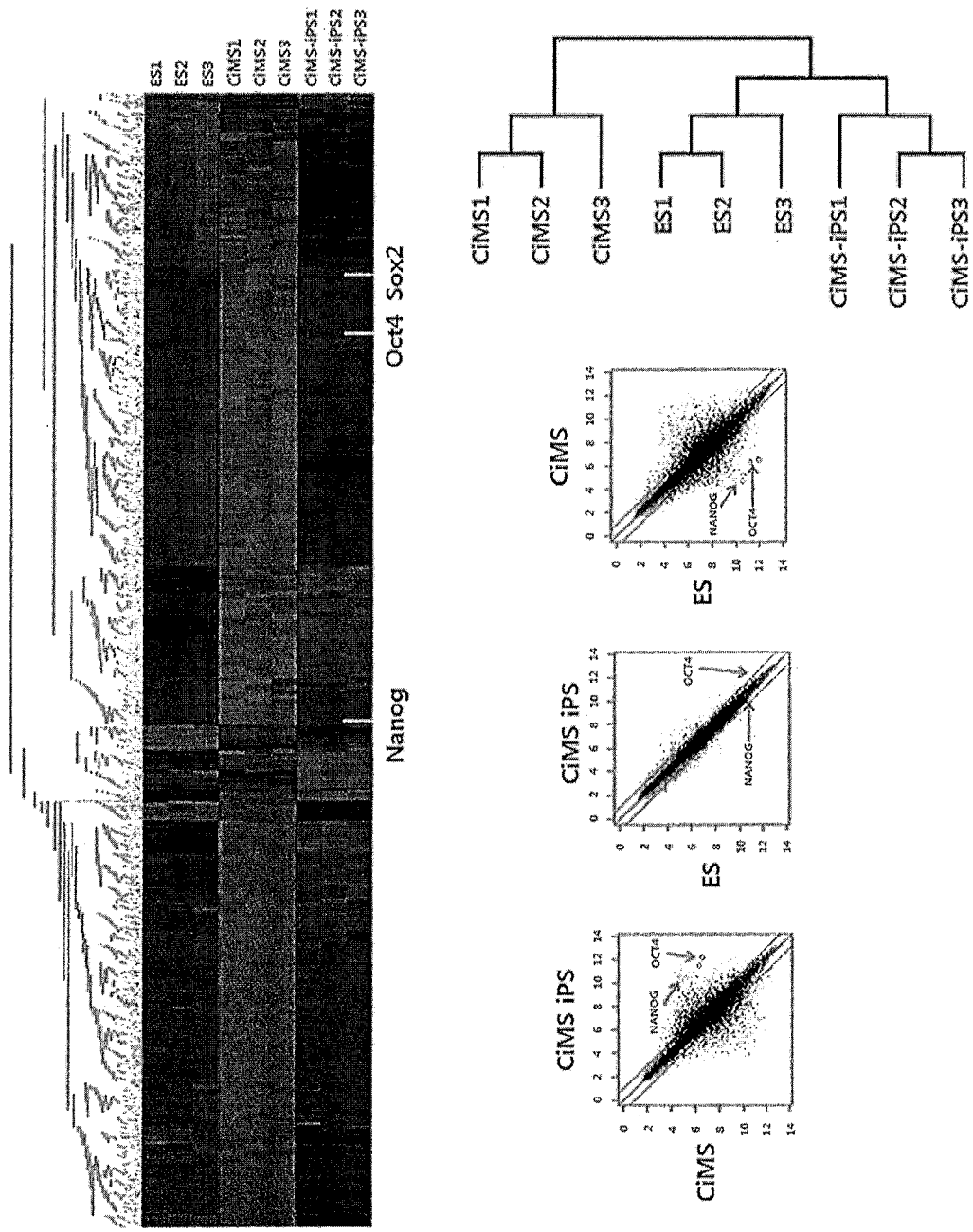

Optimized endothelial cells differentiation protocol

Number of days of EC differentiation

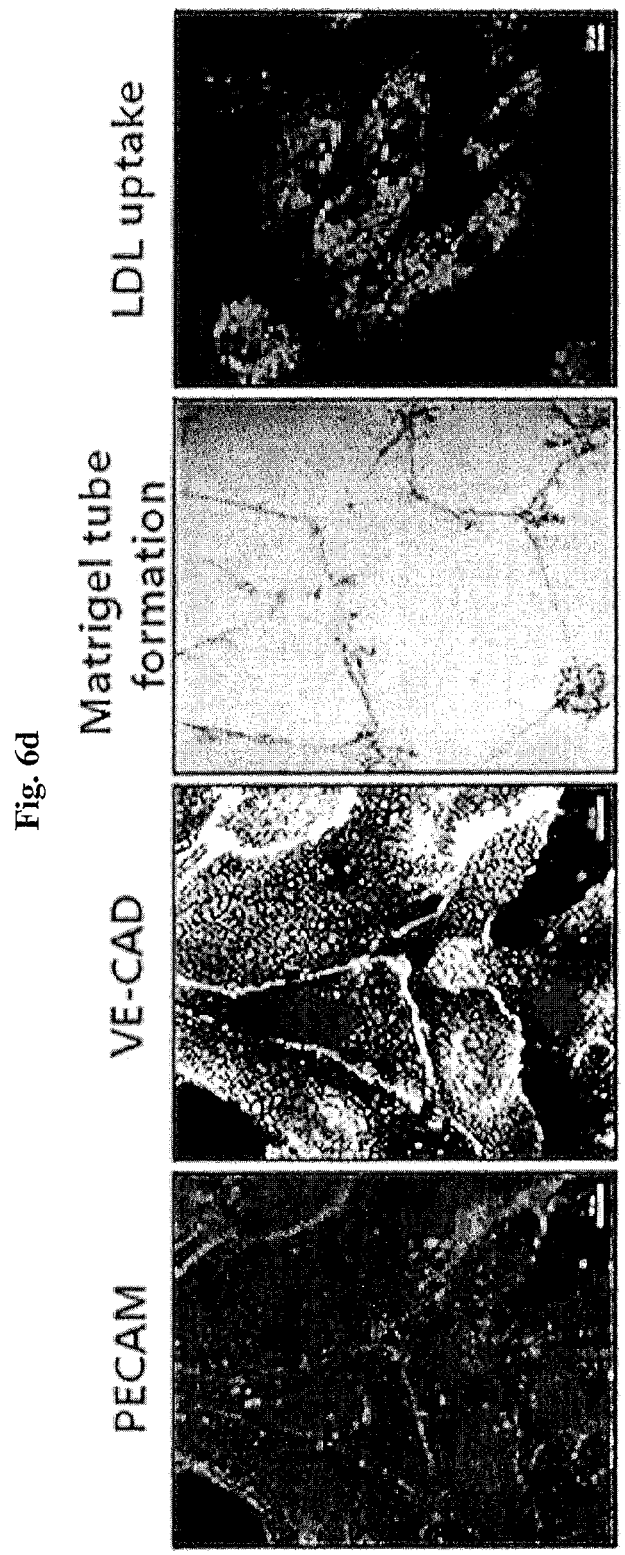

Optimized smooth muscle cells differentiation protocol

Number of days of VSMC differentiation

Protocol of differentiation of induced pluripotent stem cells into cardiomyocytes

METHOD FOR DIFFERENTIATING INDUCED PLURIPOTENT STEM CELLS, WHICH ARE PREPARED FROM ENDOCARDIUM-DERIVED ADULT STEM CELLS, INTO CARDIOVASCULAR CELLS, AND USE THEREOF

STATEMENT REGARDING GOVERNMENT RIGHTS

This study was supported by a grant of the Korea Health Technology R&D Project "Strategic Center of Cell & Bio Therapy" through the Korea Health Industry Development Institute (KHIDI), funded by the Ministry of Health & Welfare (MHW), Republic of Korea (grant number: HI-17 C-2085).

This study was supported by a grant of the Korea Health Technology R&D Project "Korea Research-Driven Hospital" through the Korea Health Industry Development Institute (KHIDI), funded by the Ministry of Health & Welfare, Republic of Korea (grant number: HI14C1277).

CROSS-REFERENCE TO RELATED APPLICATION

This application claims priority to and the benefit of Korean Patent Application No. 10-2015-0135715 filed on Sep. 24, 2015 and International Patent Application No. PCT/KR2015/012392, filed on Nov. 18, 2015, the disclosure of which is incorporated herein by reference in its entirety.

TECHNICAL FIELD

The present invention relates to a method of preparing induced pluripotent stem cells from endocardium-derived adult stem cells isolated from peripheral blood, a method of differentiating induced pluripotent stem cells prepared using the method, into cardiovascular cells, and a use thereof.

BACKGROUND ART

The development of a method of producing induced pluripotent stem cells (iPSCs) using 4 genes, developed by Professor Yamanaka of Japan in 2006, has presented a new possibility of developing a patient-customized cell therapy market and research on disease mechanisms. Thus, the development of a method of producing iPSCs using a method that does not cause genetic modification has been remarkably advanced, and the types of various patient-derived primary cells used to produce iPSCs have also been sought.

Skin fibroblasts are the most widely used cells for iPSC production, and it is easy to access and culture these skin fibroblasts. According to the findings reported to date, cells at a slightly younger stage than adult cells have high proliferative potential and special genetic makeup, i.e., stemness, and thus when used for iPSC production, the number of Yamanaka factors provided can be reduced. In particular, in the case of neural stem cells, SOX2 and c-MYC are inherently expressed, and thus it is possible to produce iPSCs therefrom only by introducing two factors, i.e., OCT4 and KLF4. Thus, when cells having stemness at a slightly younger stage than somatic cells are used as primary cells, the time for iPSC production may be shortened and production efficiency may be increased. Furthermore, if iPSCs can be established with a small number of Yamanaka factors by examining its gene expression, it may be advantageous in that when the cells are differentiated into target cells and used for treatment, a risk of developing cancer may be decreased.

In addition, as a result of various studies using murine and human cells, it has been reported that there is a difference in efficiency of differentiation from iPSCs to target cells according to primary cells. This is considered because the epigenetic memory of original somatic cells remains even after de-differentiation. Thus, from the initial stage of the production of iPSCs, primary cells should be selected in consideration of the efficiency of differentiation into target cells, cell function and stability after differentiation, and developmental origin.

According to a report in 2014, when cardiac progenitor cell-derived iPSCs (CPC-iPSCs) and fibroblast-derived iPSCs (Fib-iPSCs) were differentiated into cardiomyocytes, higher differentiation efficiency was exhibited in the case of CPC-iPSCs than in the case of Fib-iPSCs, and when comparing the cases of differentiating the same cells into endothelial cells and smooth muscle cells with each other, higher differentiation efficiency was exhibited in the case of CPC-iPSCs (Sanchez-Freire et al. 2014, JACC, 64(5):449-450). Thus, in the case of differentiating into cardiovascular cells using iPSCs, the use of primary cells may play an important role in increasing differentiation efficiency.

In addition, when basically considering the storage of primary cells, there should be no change in the composition of cells before and after storage. In addition, when considering the possibility of various applications, a method of acquiring specimens should be a non-invasive method rather than an invasive method through a biopsy which is at risk for infection, and thus it may be possible to obtain primary cells of various backgrounds such as age, gender, disease, and the like.

Taking all together into consideration, ideal conditions for becoming primary cells of iPSCs are as follows: First, sample acquisition should be easy. A large number of cells should be obtained easily and safely at the time of acquisition. Second, they should be sensitive to the introduction and expression of foreign genes. Third, they should be cells that can be isolated regardless of age, gender, ethnicity, and physical conditions of donors and when isolated, they should be cells that can represent genetic information of a donor thereof. Fourth, they should have stemness to increase the production efficiency of iPSCs, and they should be cells having the same epigenetic memory, and thus when differentiating into target cells, differentiation efficiency may be increased.

However, as a result of analysis of various cells having reported to be used for iPSCs, cells satisfying all these conditions do not exist. To compensate for this, a method of acquiring various cells from a donor has been proposed, but this requires too much labor, time, and resources for isolation, culture, and storage. Therefore, the inventors of the present invention restricted the field and tried to discover primary cells to be used in the production of iPSCs that can be used in a limited way for the treatment of cardiovascular cells.

DISCLOSURE

Technical Problem

As a result of having intensively studied to acquire and verify primary cells optimized for the production of induced pluripotent stem cells that can be used for cardiovascular cell therapy, the inventors of the present invention established a method of preparing induced pluripotent stem cells with high efficiency by using endocardium-derived adult stem cells isolated from human peripheral blood, and differentiated the prepared induced pluripotent stem cells into endothelial cells, smooth muscle cells, and cardiomyocytes, which are cardiovascular cells, thus completing the present invention.

Therefore, an object of the present invention is provide a method of preparing induced pluripotent stem cells using endocardium-derived adult stem cells, and induced pluripotent stem cells prepared thereby.

In addition, another object of the present invention is to provide a method of differentiating the induced pluripotent stem cells into endothelial cells, smooth muscle cells, and cardiomyocytes, and endothelial cells, smooth muscle cells, and cardiomyocytes obtained by the differentiation method.

In addition, still another object of the present invention is to provide a cell therapeutic agent for treating a cardiovascular disease, including endothelial cells, smooth muscle cells, or cardiomyocytes obtained by the differentiation method, as an active ingredient.

However, technical problems to be solved by the present invention are not limited to the above-described technical problems, and other unmentioned technical problems will become apparent to those of ordinary skill in the art from the following description.

Technical Solution

To achieve the above-described objects, the present invention provides a method of preparing induced pluripotent stem cells, including the following processes:

(a) introducing the sex determining region Y (SRY)-box 2 (SOX2) gene, the v-myc avian myelocytomatosis viral oncogene homolog (c-MYC) gene, the octamer-binding transcription factor 4 (OCT4) gene, and the Kruppel-like factor 4 (KLF4) gene into endocardium-derived adult stem cells;

(b) producing epithelial-like cells by culturing the gene-introduced cells while replacing the medium with an endothelial cell growth medium (EGM) every day for 8 days to 12 days; and (c) mounting the cells on feeder cells and culturing the resulting cells in an EGM for 3 days to 7 days, and then replacing the medium with an embryonic stem cell (ES) medium.

In one embodiment of the present invention, the endocardium-derived adult stem cells may be obtained by suspending and seeding peripheral blood mononuclear cells (PBMCs) isolated from peripheral blood in an EGM, and then removing T cells and culturing the resulting cells while replacing the medium for 5 days to 8 days.

In another embodiment of the present invention, the feeder cells may be a mouse-derived embryonic fibroblast cell line.

In another embodiment of the present invention, the ES medium may be Dulbecco's Modified Eagle Medium: Nutrient Mixture F-12 (DMEM/f12) treated with a knockout serum replacement, L-glutamine, non-essential amino acids, 2-mercaptoethanol, penicillin/streptomycin, and bFGF.

The present invention also provides induced pluripotent stem cells prepared by the above-described preparation method.

In one embodiment of the present invention, the induced pluripotent stem cells may exhibit the following characteristics:

(a) positive immunological characteristics for alkaline phosphatase (ALP), OCT4, Nanog homeobox (NANOG), and TRA-1-81;

(b) ability to differentiate into three germ layers in vitro and in vivo; and (c) growing while being adhered, and exhibiting morphological and genetic characteristics of embryonic stem cells.

The present invention also provides a method of differentiating induced pluripotent stem cells into endothelial cells, including the following processes:

(a) treating the induced pluripotent stem cells with a glycogen synthase kinase 3 (GSK-3) inhibitor and culturing the resulting cells for 1 day to 3 days for differentiation into mesoendodermal cells;

(b) preparing CD34 positive cells by treating the mesoendodermal cells with bone morphogenetic protein 4 (BMP4) and an Akt (protein kinase B; PKB) inhibitor for differentiation into mesoblast cells, treating the mesoblast cells with a growth factor, and culturing the resulting cells for 7 days to 10 days while replacing the medium every day; and (c) re-treating the CD34 positive cells with the growth factor and sub-culturing the resulting cells for 10 days to 20 days while replacing the medium every day.

In one embodiment of the present invention, the GSK-3 inhibitor may be 6-[[2-[[4-(2,4-dichlorophenyl)-5-(5-methyl-1H-imidazol-2-yl)-2-pyrimidinyl]amino]ethyl]amino]-3-pyridinecarbonitrile (CHIR99021).

In another embodiment of the present invention, the Akt inhibitor may be 2-(2-amino-3-methoxyphenyl)-4H-1-benzopyran-4-one (PD98059).

In another embodiment of the present invention, the growth factor may be a vascular endothelial growth factor (VEGF) and a basic fibroblast growth factor (bFGF).

The present invention also provides endothelial cells obtained by the differentiation method.

The present invention also provides a method of differentiating induced pluripotent stem cells into smooth muscle cells, including the following processes:

(a) treating the induced pluripotent stem cells with a glycogen synthase kinase 3 (GSK-3) inhibitor and culturing the resulting cells for 1 day to 3 days for differentiation into mesoendodermal cells;

(b) treating the obtained mesoendodermal cells with bone morphogenetic protein 4 (BMP4) and a phosphatidylinositol-4,5-bisphosphate 3-kinase (PI3K) inhibitor and culturing the resulting cells for 1 day to 2 days; and (c) treating the cultured mesoendodermal cells with a growth factor and sub-culturing the resulting cells for 12 days to 16 days.

In one embodiment of the present invention, the GSK-3 inhibitor may be 6-[[2-[[4-(2,4-dichlorophenyl)-5-(5-methyl-1H-imidazol-2-yl)-2-pyrimidinyl]amino]ethyl]amino]-3-pyridinecarbonitrile (CHIR99021).

In another embodiment of the present invention, the PI3K inhibitor may be 2-(4-morpholino)-8-phenyl-4H-1-benzopyran-4-one (LY294002).

In another embodiment of the present invention, the growth factor may be platelet-derived growth factor-BB (PDGF-BB) and transforming growth factor-beta (TGF-β).

The present invention also provides smooth muscle cells obtained by the above-described differentiation method.

The present invention also provides a method of differentiating induced pluripotent stem cells into cardiomyocytes, including the following processes:

(a) culturing the induced pluripotent stem cells in a medium containing a glycogen synthase kinase 3 (GSK-3) inhibitor, bone morphogenetic protein 4 (BMP4), vitamin C, activin A, and an insulin-free B27 supplement for 20 hours to 30 hours for differentiation into mesoblast cells;

(b) culturing the obtained mesoblast cells in a medium supplemented with BMP4, a growth factor, and an insulin-free B27 supplement for 2 days to 4 days; and (c) culturing the cultured mesoblast cells in a medium containing an insulin-free B27 supplement for 1 day to 2 days, adding a wingless-type MMTV integration site family (Wnt) signaling inhibitor thereto, culturing the resulting cells for 1 day to 3 days, and then further culturing the resulting cells in a medium containing an insulin-containing B27 supplement.

In one embodiment of the present invention, the GSK-3 inhibitor may be 6-[[2-[[4-(2,4-dichlorophenyl)-5-(5-methyl-1H-imidazol-2-yl)-2-pyrimidinyl]amino]ethyl]amino]-3-pyridinecarbonitrile (CHIR99021).

In another embodiment of the present invention, the growth factor may be a vascular endothelial growth factor (VEGF).

In another embodiment of the present invention, the Wnt signaling inhibitor may be N-(6-methyl-2-benzothiazolyl)-2-[(3,4,6,7-tetrahydro-4-oxo-3-phenylthieno[3,2-d]pyrimidin-2-yl)thio]-acetamide (IWP2).

The present invention also provides cardiomyocytes obtained by the above-described differentiation method.

The present invention also provides a cell therapeutic agent for treating a cardiovascular disease, including the obtained endothelial cells, smooth muscle cells, or cardiomyocytes as an active ingredient.

In one embodiment of the present invention, the cardiovascular disease may be a disease selected from the group consisting of angina pectoris, myocardial infarction, ischemic heart disease, hyperlipidemia, stroke, arteriosclerosis, hypertension, arrhythmia, cerebrovascular disease, and coronary artery disease.

The present invention also provides a method of preventing or treating a cardiovascular disease, including administering the obtained endothelial cells, smooth muscle cells, or cardiomyocytes to an individual.

The present invention also provides a use of the endothelial cells, smooth muscle cells, or cardiomyocytes obtained by the differentiation method for preventing or treating a cardiovascular disease.

Advantageous Effects

Endocardium-derived adult stem cells, which are primary cells for the production of induced pluripotent stem cells of the present invention, can be easily isolated from only a small amount of peripheral blood and cultured and have high proliferative potential, and thus can be stored without genetic variations, and the number of cells sufficient to be used for cell therapy can be rapidly secured. In addition, endocardium-derived adult stem cells have stemness, and thus exhibit higher efficiency of producing induced pluripotent stem cells through transduction of 4 types of Yamanaka factors than that of conventionally used skin fibroblasts, and have epigenetic memory of cardiovascular cells due to having an endocardial origin thereof, and thus, after producing induced pluripotent stem cells therefrom, the resulting cells can differentiate into cardiovascular cells such as endothelial cells, smooth muscle cells, cardiomyocytes, and the like with high efficiency. Thus, cardiovascular cells obtained by differentiation of the induced pluripotent stem cells can be used for library screening of a therapeutic material for the development of therapeutic agents for cardiovascular diseases and for research on mechanisms for the treatment of cardiovascular diseases. In addition, it is expected that the cardiovascular cells can be widely used in a variety of fields, such as the use thereof as a cell therapeutic agent by directly manipulating and proliferating the cells and injecting the resulting cells again into a patient.

DESCRIPTION OF DRAWINGS

FIG. 1B illustrates results showing that a process of mounting the Yamanaka factor-transduced CiMSs on feeder cells and then gradually replacing the used media with ES media was effective in producing induced pluripotent stem cells (iPSCs).

FIG. 2C illustrates comparative analysis results of overall gene expression patterns through microarray analysis to verify the undifferentiation ability of CiMS-iPSCs.

FIG. 6D illustrates results of the expression of PECAM and VE-Cadherin, which are endothelial cell expression markers, Matrigel tube formation, and LDL uptake in endothelial cells obtained by differentiation from CiMS-iPSCs.

BEST MODE

Figure 1A:
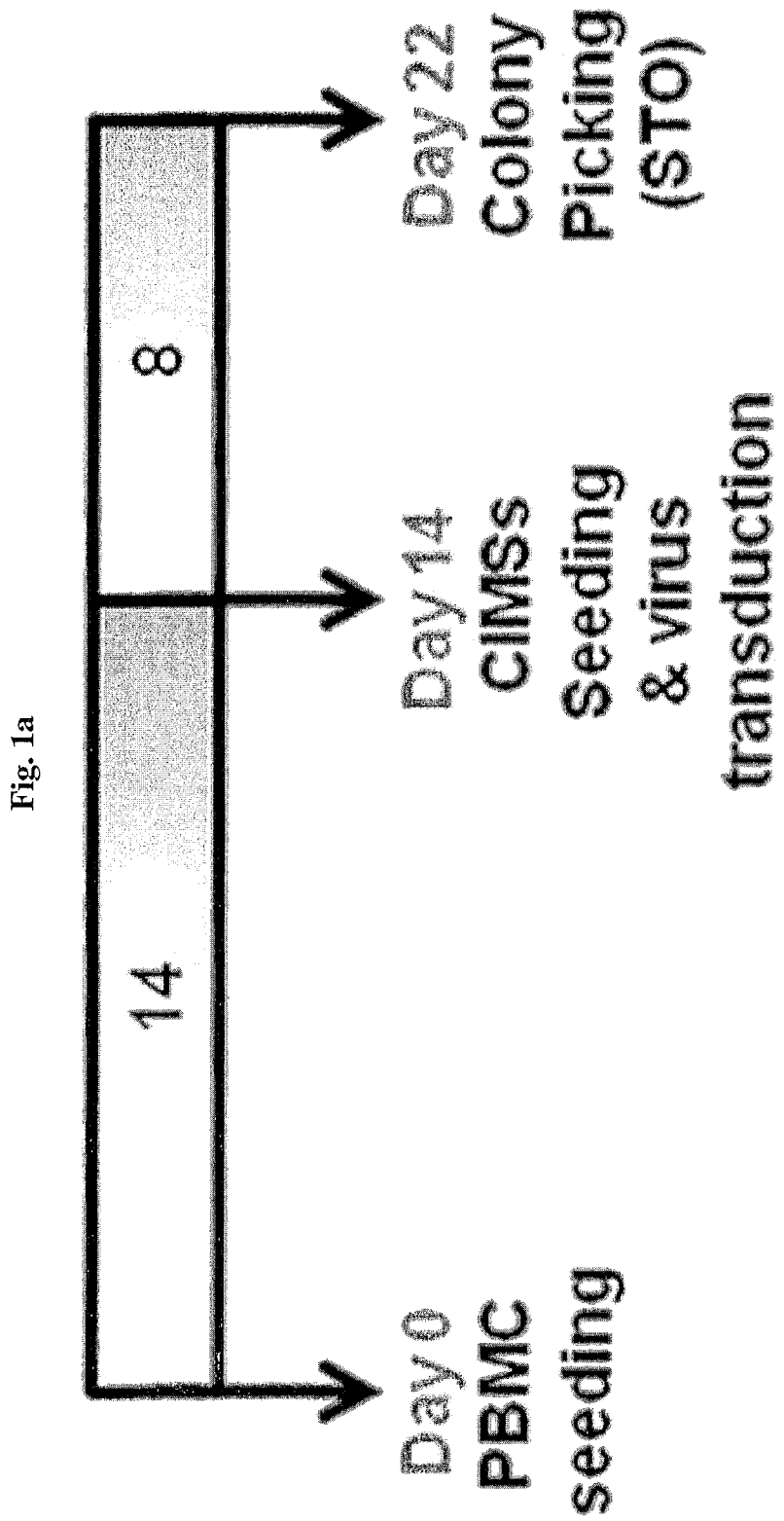
FIG. 1A illustrates a process of culturing endocardium-derived adult stem cells (CiMSs) transduced with Yamanaka factors, i.e., SOX2, c-MYC, OCT4, and KLF4, from peripheral blood mononuclear cells (PBMCs) isolated from human blood, over time.

The present invention relates to a method of preparing induced pluripotent stem cells using endocardium-derived adult stem cells isolated from peripheral blood as primary cells, a method of differentiating the induced pluripotent stem cells prepared using the method into cardiovascular cells, and a use thereof.

Therefore, the present invention provides a method of preparing induced pluripotent stem cells, including the following processes:

(a) introducing the sex determining region Y (SRY)-box 2 (SOX2) gene, the v-myc avian myelocytomatosis viral oncogene homolog (c-MYC) gene, the octamer-binding transcription factor 4 (OCT4) gene, and the Kruppel-like factor 4 (KLF4) gene into endocardium-derived adult stem cells;

(b) producing epithelial-like cells by culturing the gene-introduced cells while replacing the medium with a microvascular endothelial cell growth media-2 (EGM™-2MV BulletKit™) medium every day for 8 days to 12 days; and (c) mounting the cells on feeder cells and culturing the resulting cells in an EGM™-2MV BulletKit™ medium for 3 days to 7 days, and then replacing the medium with an embryonic stem cell (ES) medium.

The term "stem cells" as used herein refers to cells that are the foundation of cells or tissues constituting an individual, and have characteristics such as self-renewal by repeatedly dividing, and multipotency which is an ability to differentiate into cells having a specific function according to an environment. Stem cells are generated in all tissues during fetal developmental processes, and found in some tissues in which cells are actively replaced, such as bone marrow, epithelial tissues, and the like in adults. Stem cells are divided into totipotent stem cells that are formed when a first division of an embryo starts, pluripotent stem cells in an inner membrane of the blastocyst that is formed by repeated divisions of the cells, and multipotent stem cells included in mature tissues and organs, according to the type of cells that can be differentiated. In this case, the multipotent stem cells are cells that can be differentiated only into cells specific to tissues and organs including the cells, and are involved in growth and development of tissues and organs of the fetal stage, neonatal stage, and adult stage, homeostatic maintenance of adult tissues, and functions of inducing regeneration when tissues are damaged. Such tissue-specific multipotent cells are collectively referred to as adult stem cells.

The term "induced pluripotent stem cells (iPSCs)" as used herein refers to dedifferentiated stem cells, and cells that return to a pre-differentiated cell stage by transfecting differentiated somatic cells with cell differentiation-related genes and are induced to have pluripotency like embryonic stem cells. In 2006, Professor Shinya Yamanaka of Kyoto University produced stem cells with pluripotency like embryonic stem cells by introducing several genes into mouse skin fibroblasts, and successfully produced induced pluripotent stem cells by introducing genes into adult skin cells in 2007. The genes are SOX2, c-MYC, OCT4, and KLF4, which are also referred to as Yamanaka factors, and also in the present invention, to prepare induced pluripotent stem cells from endocardium-derived adult stem cells, the four types of genes were introduced.

The endocardium-derived adult stem cells of process (a) may be obtained by suspending and seeding peripheral blood mononuclear cells (PBMCs) isolated from peripheral blood in an EGM™-2MV BulletKit™ medium, and then removing T cells and culturing the resulting cells while replacing the medium every day for 5 days to 8 days. In the present invention, the endocardium-derived adult stem cells obtained by the above-described method are named circulating multipotent stem cells (CiMSs).

The term "peripheral blood" as used herein refers to blood that circulates in bodies of mammals including humans, and can be diversely extracted using arteries, veins, peripheral blood vessels, or the like.

The term "PBMC" as used herein refers to a mononuclear cell present in peripheral blood, and includes immune cells such as B cells, T cells, macrophages, dendritic cells, natural killer (NK) cells, and the like, granulocytes such as a basophil, eosinophil, and neutrophil, and the like. The PBMC may be separated using general preparation methods, for example, density gradient centrifugation using Ficoll-Paque, but the present invention is not limited thereto.

The term "gene introduction" as used herein refers to artificial introduction of a gene or a group of genes into a cell to express the group of genes, or a manipulation of inserting another gene (group) into a genome of the cell. The gene introduction may be performed by a method using a non-viral carrier such as liposome nanoparticles or a cationic polymer, a method using a viral carrier, or a physical method such as an electroporation method, preferably, a method using a virus carrier, or more preferably, a method using a retrovirus, but the present invention is not limited thereto. Retroviruses may be prepared by conventional methods using general cells known in the art. In one embodiment of the present invention, a plasmid and virus packaging vector cloned with each of the SOX2, c-MYC, OCT4, and KLF4 genes, which are referred to as Yamanaka factors, are transfected into 293T cells to produce a retrovirus expressing each of the four genes.

As used herein, so-called "feeder cells" are known to secrete nutritional factors that contribute to maintaining the undifferentiated state of embryonic stem cells and be associated with undifferentiation maintenance mechanisms mediated by cell contact. Signaling substances secreted by feeder cells contribute to regulating the undifferentiation maintenance or differentiation initiation of embryonic stem cells. The substances secreted from feeder cells may be wingless-type MMTV integration site family (Wnt) proteins, bone morphogenetic proteins (BMPs), transforming growth factor-beta (TGF-TGF-β), extracellular matrices, and the like. There are reports of differentiation into embryonic stem cells or induced pluripotent stem cells by using various feeder cells derived from mice or humans. In the present invention, a mouse-derived embryonic fibroblast cell line, preferably STO cells, is used as the feeder cells, but the present invention is not limited thereto.

In process (c), the ES medium may be a Dulbecco's Modified Eagle Medium: Nutrient Mixture F-12 (DMEM/f12) medium, preferably a DMEM/f12 medium supplemented with a knockout serum replacement, L-glutamine, non-essential amino acids, 2-mercaptoethanol, penicillin and streptomycin, and bFGF, but the present invention is not limited thereto.

In one embodiment of the present invention, the SOX2, c-MYC, OCT4, and KLF4 genes were introduced into the endocardium-derived adult stem cells according to the above method, followed by culturing while replacing the medium with an EGM™-2MV BulletKit™ medium every day. As a result, the resulting cells were transformed into epithelial-like cells from about day 2, and colonies were formed between day 8 and day 12. As a result of mounting the colonies on feeder cells and culturing the resulting cells, the colonies of induced pluripotent stem cells started to be formed from about day 15 after gene introduction, and after the colony formation, the colonies were cultured by gradually replacing the medium with an ES medium and, as a result, stabilized induced pluripotent stem cells were obtained (see Example 2-2).

In another embodiment of the present invention, as a result of observation to examine characteristics of the induced pluripotent stem cells, it was confirmed that the induced pluripotent stem cells were adhered and grown and had morphological and genetic characteristics of embryonic stem cells. In addition, as a result of verifying undifferentiation potentials, undifferentiated genes such as alkaline phosphatase (ALP), OCT4, Nanog homeobox (NANOG), TRA-1-81, and the like were confirmed to be expressed at mRNA and protein levels, and exhibited gene expression patterns very similar to that of embryonic stem cells (see Example 3). In addition, it was confirmed that the induced pluripotent stem cells had an ability of differentiating into three germ layers in vitro and in vivo (see Example 4).

In another embodiment of the present invention, as a result of verifying the production efficiency of induced pluripotent stem cells by using endocardium-derived adult stem cells, the endocardium-derived adult stem cells exhibited a higher viral transduction efficiency as compared to skin fibroblasts conventionally used in the production of induced pluripotent stem cells and 293T cells having a high gene introduction efficiency, and it was confirmed by ALP staining that induced pluripotent stem cells were prepared using endocardium-derived adult stem cells with higher efficiency than in the case of skin fibroblasts (see Example 5).

The inventors of the present invention established a method capable of differentiating induced pluripotent stem cells prepared from endocardium-derived adult stem cells by the above-described method into endothelial cells, smooth muscle cells, and cardiomyocytes with high efficiency to differentiate into cardiovascular cells having the same origin as that of primary cells, and verified the efficiency thereof.

Therefore, the present invention provides a method of differentiating induced pluripotent stem cells into endothelial cells, including the following processes:

(a) treating induced pluripotent stem cells prepared from endocardium-derived adult stem cells with a glycogen synthase kinase 3 (GSK-3) inhibitor and culturing the resulting cells for 1 day to 3 days for differentiation into mesoendodermal cells;

(b) preparing CD34 positive cells by treating the mesoendodermal cells with bone morphogenetic protein 4 (BMP4) and an Akt (protein kinase B; PKB) inhibitor for differentiation into mesoblast cells, treating the mesoblast cells with a growth factor, and culturing the resulting cells for 7 days to 10 days while replacing the medium every day; and (c) re-treating the CD34 positive cells with the growth factor and sub-culturing the resulting cells for 10 days to 20 days while replacing the medium every day.

In process (a), 6-[[2-[[4-(2,4-dichlorophenyl)-5-(5-methyl-1H-imidazol-2-yl)-2-pyrimidinyl]amino]ethyl]amino]-3-pyridinecarbonitrile (CHIR99021) may be used as the GSK-3 inhibitor to increase dedifferentiation efficiency, preferably CHIR99021 diluted in a B27-containing RPMI1640 medium, but the present invention is not limited thereto. In addition, the mesoendodermal cells may be preferably Brachyury T positive cells.

In process (b), the Akt inhibitor may be preferably 2-(2-amino-3-methoxyphenyl)-4H-1-benzopyran-4-one (PD98059), the growth factor may be preferably a vascular endothelial growth factor (VEGF) and a basic fibroblast growth factor (bFGF), and treatment of the growth factor may be appropriately adjusted such that the number of CD34 positive cells can increase, preferably for 7 days to 10 days, and more preferably for 7 days to 8 days.

The method may further include, before process (c), isolating only the CD34 positive cells. The process may be performed using a method selected from the group consisting of magnetic-activated cell sorting (MACS), fluorescence-activated cell sorting (FACS), IsoFaft, and DEPArray, preferably the MACS method, but the isolation method may be appropriately selected from general methods by those of ordinary skill in the art as long as it is capable of isolating only the CD34 positive cells.

In process (c), more particularly, the CD34 positive cells may be cultured by being suspended in VEGF and bFGF-retreated endothelial cell growth media (EGM) and inoculated in a Matrigel-coated plate, and when differentiated into endothelial progenitor cells, the cells may be sub-cultured while replacing the media every day for 10 days to 20 days, more preferably 10 days to 15 days, thereby obtaining mature endothelial cells.

In another embodiment of the present invention, endothelial cells obtained by differentiation of induced pluripotent stem cells prepared from endocardium-derived adult stem cells were obtained through the above-described method, the endothelial cells exhibited a pattern and total nitric oxide content similar to those of human umbilical vein endothelial cells (HUVECs) and expressed PECAM and VE-Cadherin, which are endothelial cell expression markers, and differentiation into endothelial cells was confirmed through Matrigel tube formation and low density lipoprotein (LDL) uptake (see Examples 7-1 and 7-2).

The present invention also provides a method of differentiating induced pluripotent stem cells into smooth muscle cells, including the following processes:

(a) treating induced pluripotent stem cells prepared from endocardium-derived adult stem cells with a glycogen synthase kinase 3 (GSK-3) inhibitor and culturing the resulting cells for 1 day to 3 days for differentiation into mesoendodermal cells;

(b) treating the obtained mesoendodermal cells with bone morphogenetic protein 4 (BMP4) and a phosphatidylinositol-4,5-bisphosphate 3-kinase (PI3K) inhibitor and culturing the resulting cells for 1 day to 2 days; and (c) treating the cultured mesoendodermal cells with a growth factor and sub-culturing the resulting cells for 12 days to 16 days.

Process (a) of differentiating into mesoendodermal cells from the induced pluripotent stem cells may be performed in the same manner as in the method of differentiating into endothelial cells, and the mesoendodermal cells may be Brachyury T positive cells.

In process (b), the PI3K inhibitor may be preferably 2-(4-morpholino)-8-phenyl-4H-1-benzopyran-4-one (LY294002), but the present invention is not limited thereto.

In process (c), the growth factor may be preferably platelet-derived growth factor-BB (PDGF-BB) and transforming growth factor-beta (TGF-β), and smooth muscle progenitor cells differentiated after growth factor treatment may be inoculated in a type II collagen-coated dish and sub-cultured for 12 days to 16 days, more preferably for 14 days to 16 days, thereby obtaining mature smooth muscle cells.

In another embodiment of the present invention, smooth muscle cells differentiated from induced pluripotent stem cells prepared from endocardium-derived adult stem cells were obtained through the above-described method, and when compared to human gastric vascular smooth muscle cells (hVSMCs) as a positive control, as a result of verifying the expression of smooth muscle cell marker genes through immunofluorescence staining and Western blotting, the CNN1 (calponin) and SMA proteins were expressed at almost similar levels to those of the positive control cells, and the mRNA expression of the marker genes and the SM22a gene was confirmed from RT-PCR as well (see Example 7-3).

The present invention also provides a method of differentiating induced pluripotent stem cells into cardiomyocytes, including the following processes: (a) culturing induced pluripotent stem cells prepared from endocardium-derived adult stem cells in a medium containing a glycogen synthase kinase 3 (GSK-3) inhibitor, bone morphogenetic protein 4 (BMP4), vitamin C, activin A, and an insulin-free B27 supplement for 20 hours to 30 hours for differentiation into mesoblast cells;

(b) culturing the resulting mesoblast cells in a medium supplemented with BMP4, a growth factor, and an insulin-free B27 supplement for 2 days to 4 days; and (c) culturing the cultured cells in a medium containing an insulin-free B27 supplement for 1 day to 2 days, adding a Wnt signaling inhibitor thereto, culturing the resulting cells for 1 day to 3 days, and then further culturing the resulting cultured cells in a medium containing an insulin-containing B27 supplement.

Process (a) may proceed in such a way that the induced pluripotent stem cells are in the form of an embryonic body. After removing the induced pluripotent stem cells from feeder cells with dispase, the induced pluripotent stem cells may be cultured in an insulin-free B27 supplement and an RPMI1640 medium (primary medium) containing a glycogen synthase kinase 3 (GSK-3) inhibitor, bone morphogenetic protein 4 (BMP4), vitamin C, and activin A for 20 hours to 30 hours, more preferably for 24 hours to thereby differentiate into mesoblast cells.

The GSK-3 inhibitor may be preferably CHIR99021, but the present invention is not limited thereto.

The mesoblast cells obtained through process (a) may be cultured in a RPMI1640 medium (secondary medium) supplemented with an insulin-free B27 supplement, a low concentration of BMP4, and a growth factor for 2 days to 4 days, preferably 3 days to thereby differentiate into myocardial progenitor cells. The growth factor may be preferably a vascular endothelial growth factor (VEGF), but the present invention is not limited thereto.

In process (c), the cells cultured through process (b) may be rinsed with a RPMI1640 medium (tertiary medium) containing an insulin-free B27 supplement, culturing the resulting cells for 1 day to 2 days, preferably 1 day, adding a Wnt signaling inhibitor thereto, culturing the resulting cells for 1 day to 3 days, preferably 2 days, replacing the medium with an RPMI1640 medium (quaternary medium) containing an insulin-containing B27 supplement, and further culturing the resulting cells, thereby obtaining beating cardiomyocytes.

The Wnt signaling inhibitor of process (c) may be preferably N-(6-methyl-2-benzothiazolyl)-2-[(3,4,6,7-tetrahydro-4-oxo-3-phenylthieno[3,2-d]pyrimidin-2-yl)thio]-acetamide (IWP2), but the present invention is not limited thereto.

In another embodiment of the present invention, cardiomyocytes differentiated from induced pluripotent stem cells prepared from endocardium-derived adult stem cells were obtained through the above-described method, and as a result of microscopic observation, were confirmed to be beating embryonic bodies (see Example 7-4).

Another embodiment of the present invention provides a cell therapeutic agent for treating a cardiovascular disease, including, as an active ingredient, endothelial cells, smooth muscle cells, or cardiomyocytes obtained using the above-described differentiation method.

The cardiovascular disease may be a disease selected from, but not limited to, angina pectoris, myocardial infarction, ischemic heart disease, hyperlipidemia, stroke, arteriosclerosis, hypertension, arrhythmia, cerebrovascular disease, and coronary artery disease.

Hereinafter, exemplary embodiments will be described to aid in understanding of the present invention. However, the following examples are provided only to more easily understand the present invention, and are not intended to limit the scope of the present invention.

EXAMPLES

Example 1. CiMS Culturing Using Peripheral Blood

Peripheral blood mononuclear cells (PBMCs) were separated from human blood using Ficoll-Paque, suspended in an EGM™-2MV BulletKit™ medium (Lonza; Basel, Switzerland), and distributed into a 6-well plate coated with 10 µg/ml of fibronectin such that each well had $4 \times 10^6$ cells/ml, and then incubated in a 5% $CO_2$ incubator. On the next day, the plate was vigorously shaken several times and floating cells were removed through strong suctioning, and then replacement with a new medium and culturing were repeated for 7 days, and after 7 days, the medium was replaced once every two days. As a result, the appearance of circulating multipotent adult stem cells (CiMSs), which are endocardium-derived adult stem cells, was identified between day 5 and day 8, and the CiMSs proliferated while forming colonies within 2 weeks. These colonies were sub-cultured using 0.05% trypsin/EDTA or suspended in a fetal bovine serum (FBS) stock medium containing 10% dimethyl sulfoxide (DMSO), put into an isopropanol freezing container, left at −70° C. for 24 hours, and then lyophilized at −190° C.

Example 2. Production of Induced Pluripotent Stem Cells Using CiMSs 2-1. Retrovirus Production A retrovirus expressing each of the four genes, i.e., SOX2, c-MYC, OCT4, and KLF4, which are referred to as Yamanaka factors, was produced to be used for the production of induced pluripotent stem cells.

For this, 293T cells were cultured in a high glucose DMEM containing 10% FBS and an antibiotic until reaching 90% confluence. Meanwhile, 800 μl of a basal DMEM medium was dispensed into 1.5 ml eppendorf tubes, a plasmid cloned with one of the prepared four genes and packaging vectors, i.e., pVSV-G and pGag-Pol, were added in an amount of 10 μg/plasmid and mixed, 60 μl of a 1 mg/ml polyethyleneimine (PEI) stock was added to each tube and satisfactorily mixed therein, and the resulting mixture was maintained at room temperature for 30 minutes. To increase transfection efficiency, 293T cells were rinsed twice with 5 ml of a basal DMEM, and 10 ml of an antibiotic-free high glucose DMEM (containing 10% FBS) was added thereto, and the resulting cells were stored in an incubator at 37° C. in an antibiotic-removed state. A plasmid DNA-PEI mixed solution was prepared, the 293T cells from which an antibiotic had been removed were taken out after 30 minutes, the plasmid DNA-PEI mixed solution according to each of the four genes was mixed once gently using a pipette, and then each plasmid DNA-PEI mixed solution was added dropwise onto the 293T cells to be transfected. After 18 hours, the transfected 293T cells were taken out from the incubator and washed twice with 5 ml of a basal DMEM warmed to 37° C. to remove any excess plasmid DNA-PEI mixed solution, 10 ml of a high glucose DMEM containing 10% PBS and an antibiotic was added newly thereto, and then the resulting 293T cells were incubated in an incubator at 37° C. At this time, attention was paid to prevent the cells from falling. To recover the retrovirus produced after 48 hours, only the medium of 293T cells was collected in a 15 ml tube and centrifuged at 2,500 rpm for 15 minutes to collect only a supernatant not including separated cells and residues precipitated on the bottom, and then the supernatant was filtered through a 0.22 μm filter, followed by ultracentrifugation at 25,000 rpm and 4° C. for 1.5 hours, thereby concentrating the retrovirus included in the supernatant. The retrovirus expressing each of the four genes, precipitated in the form of a pellet, was resuspended in 100 μl of an EBM-2 medium and stored at −70° C. until use.

Example 2-2. Production and Culturing of CiMS-derived Induced Pluripotent Stem Cells One day before treatment with the retrovirus produced according to Example 2-1, the CiMSs obtained using the method of Example 1 were treated with 0.05% trypsin, separated from a culture container, and distributed into a 6-well plate at a density of $5\times10^5$ cells per well, and then the medium was replaced with a 2 ml medium on the following day. 4 hours after medium replacement, the resulting cells were treated with the retrovirus of Example 2-1 and polybrene at a concentration of 10 μg/ml and transduced therewith at 37° C. for 18 hours or more. Subsequently, the medium was replaced with a new EGM™-2MV BulletKit™ medium, followed by replacement with a medium every day and observation.

As a result, slow morphological conversion of the CiMSs into epithelial-like cells was seen from about 2 days after transduction, and colony formation was confirmed between day 8 and day 12. While observing the colony with a microscope, tips of the colony were mounted on new feeder cells treated with mitomycin C, or the total transduced CiMSs were removed with 0.05% trypsin and mounted on feeder cells at a density of $5\times10^4$ cells/well, and then continued to be cultured. The medium was replaced with an EGM™-2MV BulletKit™ medium every day until the epithelial-like cells formed colonies again. A process of obtaining CiMSs from PBMCs, mounting the CiMS colonies on feeder cells, and culturing the resulting cells, over time, is illustrated in FIG. 1A.

Meanwhile, the feeder cells were prepared one day before mounting the four gene-transduced cells thereon. For this, STO cells, which are mouse embryonic fibroblasts, were treated with mitomycin C so that a concentration became 10 μg/ml, washed with PBS for 2.5 hours, and then separated from a culture container by treatment with 0.05% trypsin. The separated cells were centrifuged at 900 rpm and 4° C. for 5 minutes, and then distributed into a 6-well plate coated with 0.1% gelatin at a density of $2.6\times10^5$ cells/well to be used. Before being mounted on the feeder cells, the four gene-transduced CiMSs were rinsed with an EBM-2 medium and the medium was replaced with an EGM™-2MV BulletKit™ medium.

As illustrated in FIG. 1B, when the four gene-transduced CiMSs mounted on the feeder cells gathered together and formed epithelial-like cell colonies, the medium was replaced with a mixture of an embryonic stem cell (ES) medium and an EGM™-2MV BulletKit™ medium in a ratio of 1:1. On the next day, the colonies were slowly adapted to the ES medium while increasing the amount of the ES medium so that a ratio of the ES medium to the EGM™-2MV BulletKit™ medium became 1.5:0.5. The composition of the ES medium was based on DMEM/f12 containing 20% knockout serum replacement, 2 mM L-glutamine, $1\times10^{-4}$ M non-essential amino acids, $1\times10^{-4}$ M 2-mercaptoethanol, and 50 units and 50 mg/ml of penicillin/streptomycin, and the ES medium was used by adding 10 ng/ml of a basic fibroblast growth factor (bFGF).

Figure 1C:
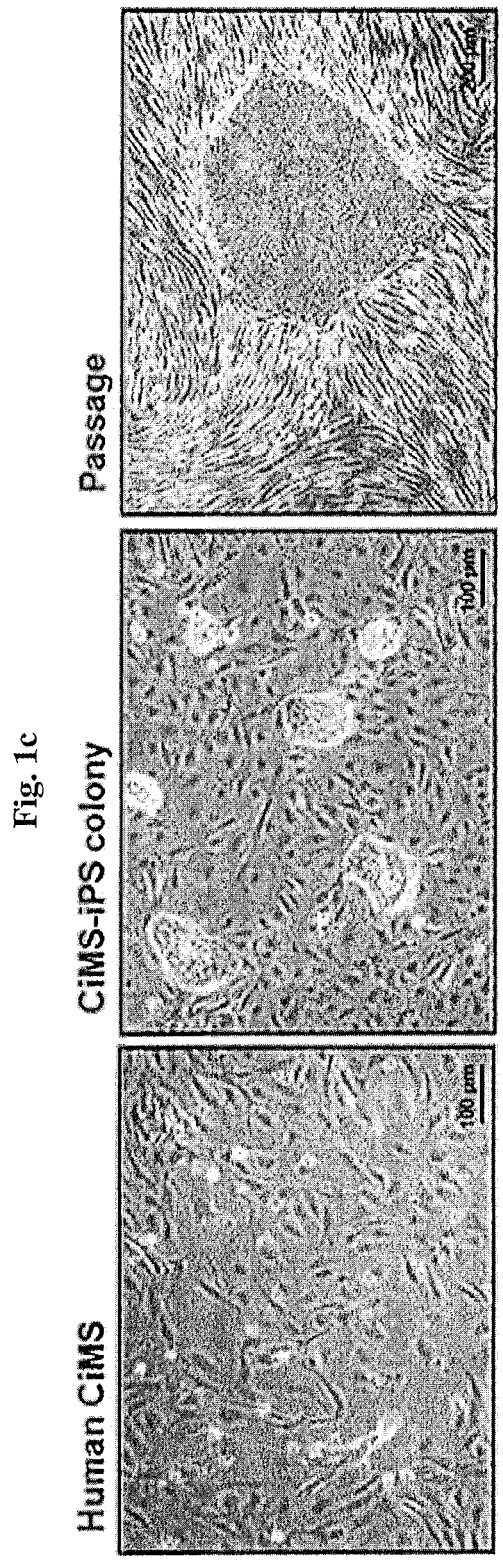
FIG. 1C illustrates microscopic images of CiMSs isolated from peripheral blood of a donor and cultured (left), a colony formed 8 days after transduction with Yamanaka factors (middle), and CiMS-derived iPSCs (CiMS-iPSCs) being cultured on feeder cells (right).

When the medium of the four gene-transduced CiMS colony mounted on the feeder cells was replaced with an ES medium every day, colonies of CiMS-derived induced pluripotent stem cells (hereinafter, referred to as CiMS-iPSCs) started to be formed as soon as day 15 after transduction. The appropriately sized CiMS-iPSC colonies were removed while being observed using a microscope, loaded onto new STO cells treated with mitomycin C, and then pipetted with a 1 ml pipette to split the colonies into an appropriate size. On the first day of passage, 10 μM trans-4-[(1R)-1-aminoethyl]-N-4-pyridinylcyclohexanecarboxamide dihydrochloride (Y-2762), which is a ROCK inhibitor, was added to the medium to increase adhesion efficiency of the colonies. By continuously sub-culturing the CiMS-iPSC colonies using the method until the CiMS-iPSC colonies were stabilized, stabilized CiMS-iPSC colonies illustrated as a microscopic image in FIG. 1C may be obtained.

Example 2-3. Production of CiMS-iPSC Frozen Stock

When the CiMS-iPSC line was established, frozen stocks were prepared for various passages. For this, colonies of 3 wells or more (30 colonies or more/well) of a 6-well plate were secured and frozen stock production was performed thereon to obtain good efficiency when the frozen stocks were thawed later. For the production of frozen stocks, dispase was mixed with a bFGF-free ES medium to a concentration of 0.5 mg/ml, followed by filtration through a 0.22 μm filter, thereby preparing a dispase solution. The medium was then removed from the CiMS-iPSCs while being cultured and 1 ml of the dispase solution was added to each well. The cells were incubated in a 37° C. incubator for 30 minutes to 1 hour, and when the colonies floated away from the feeder cells, they were wiped with 1 ml of an ES medium to prevent the colonies from being broken and collected in a 15 ml tube. In addition, the ES medium was added to wipe the remaining CiMS-iPSC colonies and after collecting all the CiMS-iPSC colonies, the colonies were centrifuged at 300×g and room temperature for 5 minutes. After centrifugation, the supernatant was removed and the CiMS-iPSC pellet was suspended in 1 ml of mFreSR™ (Stemcell Technologies), which had been cooled at room temperature, such that the colonies were not broken to a maximum extent, and put in stock tubes (cryovials). The tubes containing the cells were transferred to a freezing container containing isopropanol, stored at −70° C. overnight, and then moved to a liquid nitrogen tank ($LN_2$ tank) on the following day for long-term storage.

Example 3. Verification of Undifferentiation Potential of CiMS-iPSCs 3-1. Examination of Protein Expression of Undifferentiation Marker Gene Alkaline phosphatase (ALP) staining was performed to verify the undifferentiation potential of CiMS-iPSCs prepared according to the methods of Examples 1 and 2, and the protein expression of undifferentiation markers, i.e., the Oct4, Nanog, and Tra-1-81 genes, was examined through immunofluorescence staining.

For ALP staining, staining was performed using a BCIP/NBT substrate system manufactured by DAKO. Specifically, a dish used to culture CiMS-iPSCs was rinsed twice with PBS, 2 ml of a 1% paraformaldehyde solution diluted in PBS was added to the dish, and the cells were maintained at room temperature for 10 minutes to be immobilized. After rinsing twice with PBS, the BCIP/NBT substrate system was dropped to cover the cells, and then shielded from light and allowed to react on a rocker at room temperature while being mixed for 30 minutes so as not to be dried.

Next, to perform immunofluorescence staining, the CiMS-iPSC-cultured dish was rinsed twice with PBS, 1 ml of 100% cold methanol stored at −20° C. was added to the dish, and the cells were immediately transferred to the −20° C. dish and maintained for 10 minutes to immobilize the cells. After 10 minutes, the cells were removed and the methanol was discarded, and the cells were rinsed three times with 0.05% TBS-T (1×TBS: Tris-Buffered Saline, 0.05% Tween 20) each for 5 minutes and then an area thereof to be stained was marked as a circle with a Dako pen. Then, a blocking solution prepared by dissolving 1% bovine serum albumin (BSA) and 0.05% Triton X-100 in PBS and filtering the resulting solution through a 0.22 μm filter was applied to cover the area marked not to be dried, and then blocked at room temperature for 30 minutes. Next, a primary antibody against the undifferentiation markers Oct4, Nanog, or Tra-1-81 was diluted 1:100 in a dilution solution to prepare a primary antibody solution, the blocking solution was removed, the area was treated with the primary antibody solution and was allowed to react at 4° C. overnight. On the next day, the cells were rinsed three times with 0.05% TBS-T each for 10 minutes, and then a second antibody solution (1:100) corresponding to each antibody was prepared so that the cells did not dry out, and the cells were treated with the secondary antibody solution, shielded from light at room temperature, and allowed to react for 2 hours. Thereafter, the cells were rinsed three times with 0.05% TBS-T for 10 minutes at room temperature, and then for nucleus staining, 1 mg/ml of a 4',6-diamidino-2-phenylindole (DAPI) solution was mixed in a dilution solution to 1:1000, the resulting solution was added to the cells, followed by light shielding and reaction at room temperature for 10 minutes. It was confirmed by a fluorescence microscope that the nuclei were stained with DAPI, and the cells were rinsed three times with 0.05% TBS-T, and then mounted on a fluorescence mounting medium (manufactured by DAKO) using a cover slip.

Figure 2A:
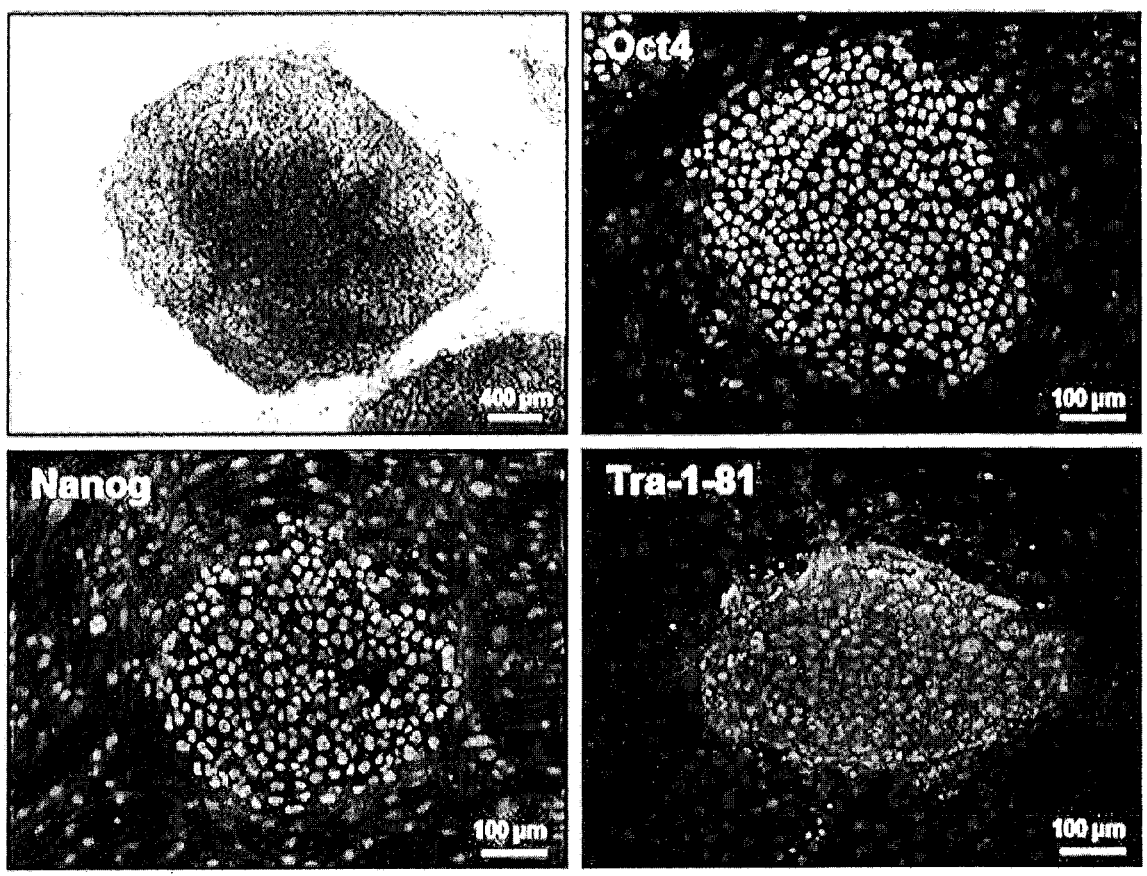
FIG. 2A illustrates verification results of the protein expression of undifferentiation marker genes through alkaline phosphatase (ALP) staining and immunofluorescent staining to verify the undifferentiation ability of CiMS-iPSCs.

As a result of observation with an optical microscope, as illustrated in FIG. 2A, it was confirmed that CiMS-iPSCs were stained with a deep purple color when ALP staining was performed, and as a result of immunofluorescence staining, it was confirmed by green fluorescence that Oct4 and Nanog were expressed in the nuclei of the CiMS-iPSC colonies and Tra-1-81 was expressed in the cell membrane.

3-2. Examination of mRNA Expression of Undifferentiation Marker Gene

Reverse transcription-polymerase chain reaction (RT-PCR) and microarray analysis were performed to examine the expression of more various undifferentiated genes in CiMS-iPSCs.

To perform RT-PCR, RNAs were extracted from four types of CiMS-iPSCs (CiMS-iPSC1, 2, 3, and 4), embryonic stem cells, and CiMSs, which are primary cells, followed by RT-PCR, and mRNA expression levels of the Oct3/4, Sox2, KLF4, c-Myc, Nanog, Nodal, REX1, DNMT, ECAT4, ECAT15, FGF4, GABR3, GAL, GDF3, PH34, TDGF1, and UTF1 genes in the cells were observed.

Figure 2B:
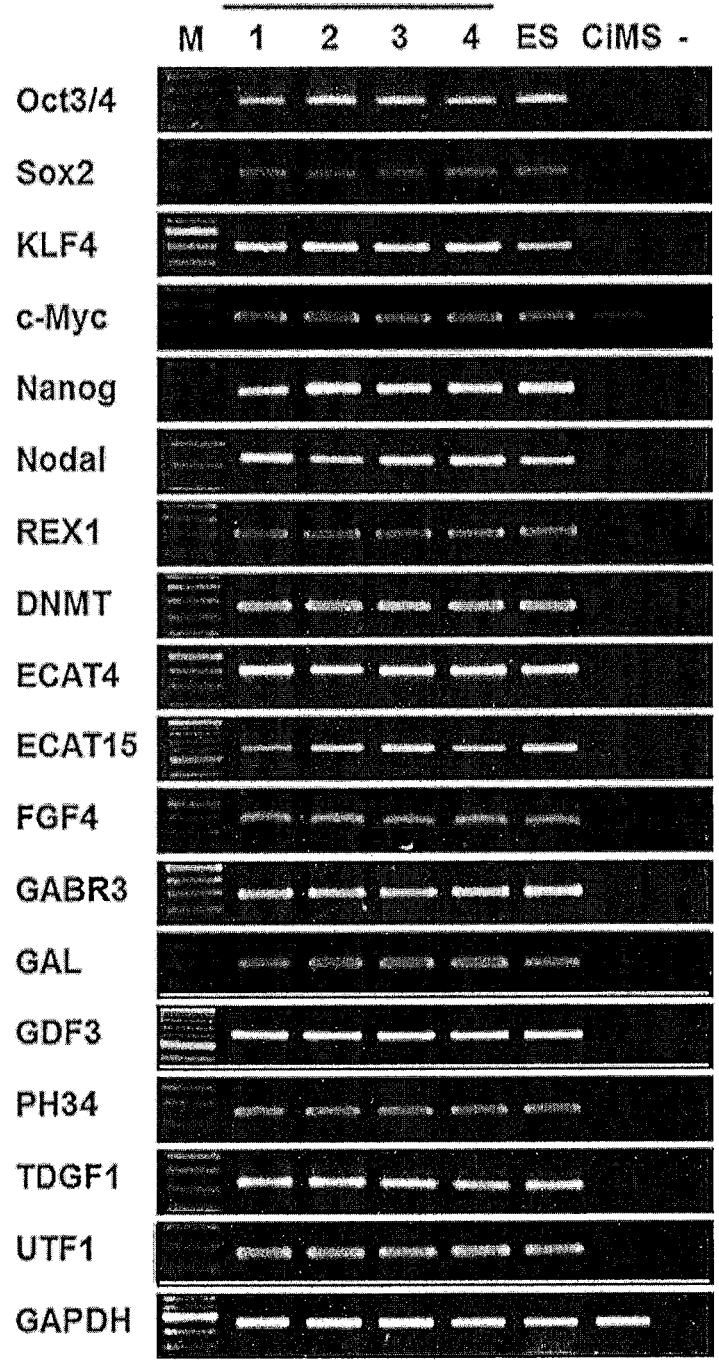
FIG. 2B illustrates verification results of mRNA expression levels of undifferentiation marker genes through RT-PCR to verify the undifferentiation ability of CiMS-iPSCs.

As a result, as illustrated in FIG. 2B, it was confirmed that the undifferentiated genes were expressed in the CiMS-iPSCs at high levels that were almost the same as those in embryonic stem cells (ES), whereas the genes were hardly expressed in the CiMSs, which are primary cells.

Next, RNAs were extracted from three types of CiMS-iPSCs (CiMS-iPSC1, CiMS-iPSC2, and CiMS-iPSC3), three types of embryonic stem cells (ES1, ES2, and ES3), and three types of CiMSs (CiMS1, CiMS2, and CiMS3), which are primary cells, and then microarray analysis was performed thereon to compare and analyze overall gene expression patterns.

As a result, as illustrated in FIG. 2C, it was confirmed that the CiMS-iPSCs exhibited almost the same gene expression pattern as ESs, whereas the CiMSs, which are primary cells, exhibited a gene expression pattern different from those of the two types of cells.

Example 4. Verification of Tridermal Differentiation Ability of CiMS-iPSCs

Undifferentiated cells such as embryonic stem cells are capable of differentiating into three germ layers, i.e., endoderm, mesoderm, and ectoderm, in vitro and in vivo, and are particularly capable of forming a teratoma in vivo. Thus, it was examined whether the CiMS-iPSCs produced according to Examples 1 and 2 had a tridermal differentiation ability.

4-1. Identification of Tridermal Differentiation Ability of CiMS-iPSCs In Vitro To examine the ability of differentiating into three germ layers in vitro, embryonic bodies (EBs) were produced from CiMS-iPSCs with 0.5 U/ml of dispase and induced to spontaneously differentiate while maintained in a bFGF-free ES medium for a long period of time. Cells being cultured as EBs were incubated for 1 week in a floating state and further incubated for 2 weeks by being attached to a 0.5% gelatin-coated dish, followed by immunofluorescence staining, and it was observed using a confocal microscope whether alpha-fetoprotein (AFP), which is an endodermal marker, α-sarcomeric actin (α-SA) and smooth muscle actin (SMA), which are mesodermal markers, and nestin, glial fibrillary acidic protein (GFAP), and β-III tubulin, which are ectodermal markers, were expressed.

Figure 3A:
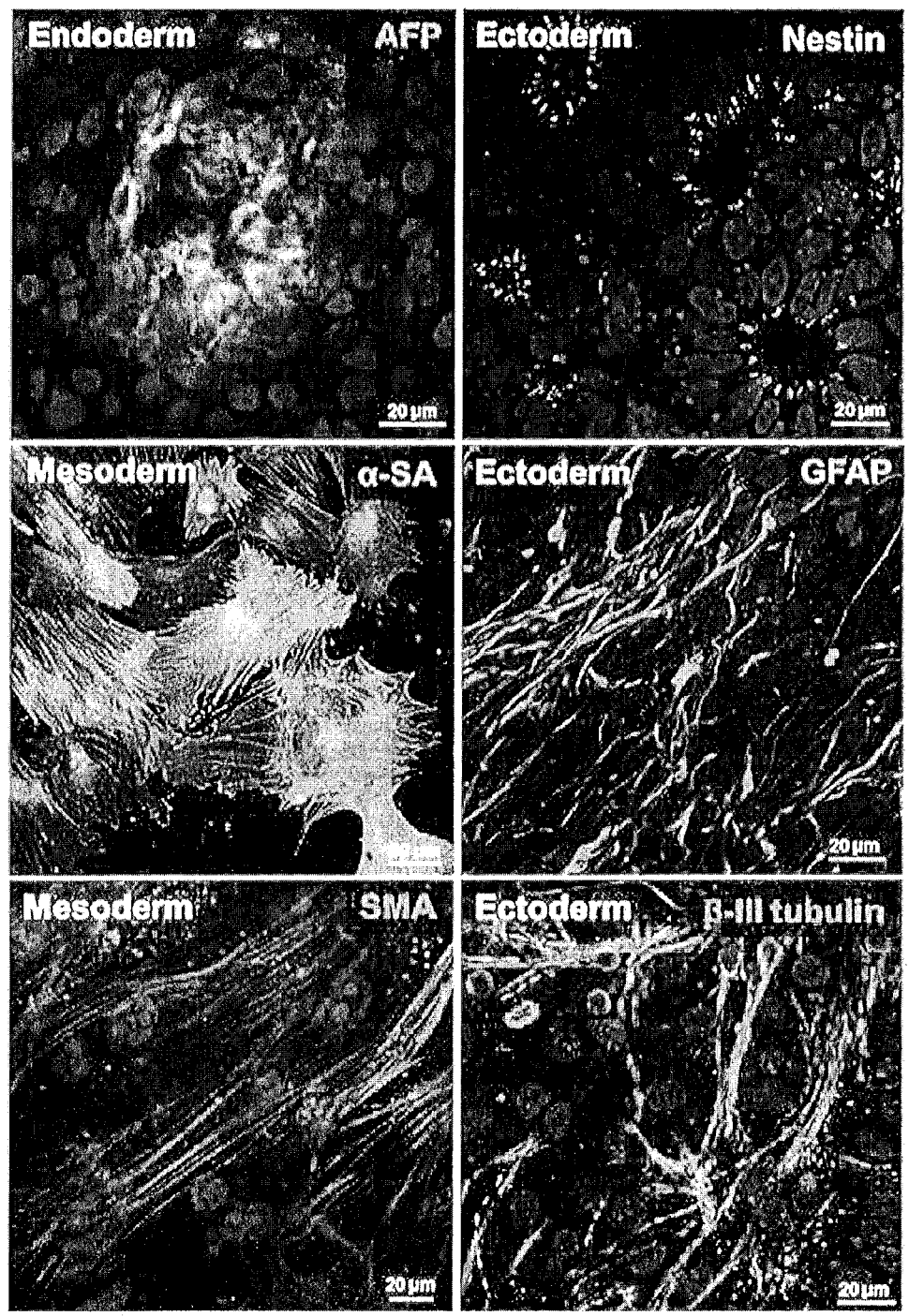
FIG. 3A illustrates verification results of the protein expression of tridermic marker genes through immunofluorescence staining to verify an ability of CiMS-iPSCs to differentiate into three germ layers in vitro.

As a result, as illustrated in FIG. 3A, it was confirmed that all the endodermal, mesodermal, and ectodermal markers were expressed in CiMS-iPSCs. From the above results, it was confirmed that CiMS-iPSCs had the ability to differentiate into three germ layers, i.e., pluripotency, similarly to embryonic stem cells.

In addition, CiMS-iPSCs were prepared using the same method as described above, and RNAs were extracted from differentiated CiMS-iPSCs (D) and undifferentiated CiMS-iPSCs (U) under culturing conditions for differentiation into three germ layers, and then expression amounts of the differentiation markers for each of the three germ layers (endoderm: AFP and GATA4, mesoderm: TnTc and Brachyury T, ectoderm: BMP4 and Ncam1) were observed.

Figure 3B:
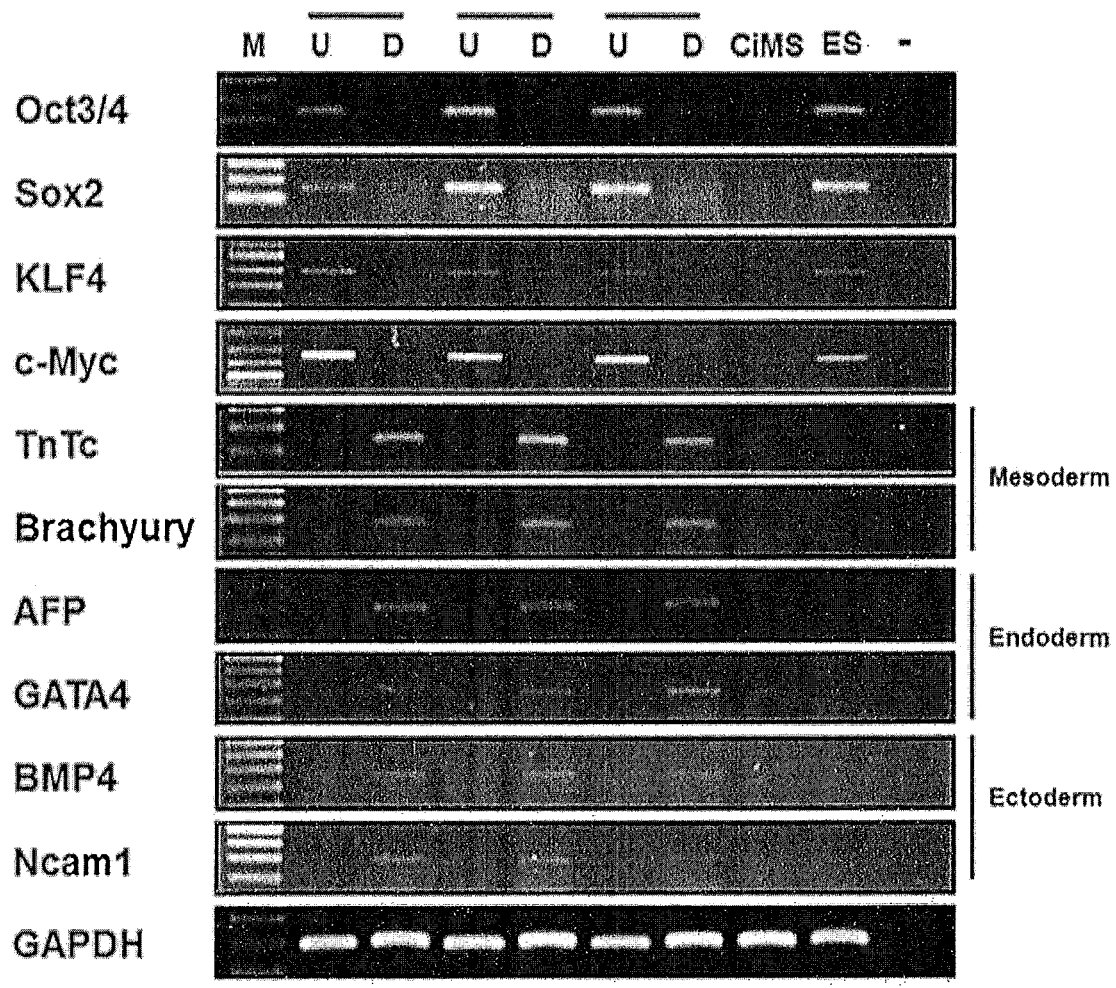
FIG. 3B illustrates comparative analysis results of mRNA expression levels of tridermic marker genes in undifferentiated or differentiated CiMS-iPSCs to verify an ability of CiMS-iPSCs to differentiate into three germ layers in vitro.

As a result, as illustrated in FIG. 3B, it was confirmed that the differentiation markers for each of the three germ layers were expressed in the differentiated CiMS-iPSCs, which indicates that the CiMS-iPSCs had the ability to differentiate into three germ layers through genetic expression.

4-2. Verification of In Vivo Tridermic Differentiation Ability of CiMS-iPSCs To perform an in vivo teratoma formation experiment, CiMS-iPSCs were treated with 0.5 U/ml of dispase to be separated from feeder cells, and the cells were collected in a 15 ml tube and centrifuged to obtain a pellet. The pellet was mixed with Matrigel on ice and Matrigel-CiMS-iPSCs were injected into the abdominal cavity of the right and left abdomen of NOD-SCID mice and observed for more than 12 weeks. When the teratomas were grown to a certain size or more, the teratomas were removed from the mice, cut into appropriate sizes, immersed in 4% paraformaldehyde to be fixed, and then were formed into paraffin blocks, followed by cutting into tissue slide sections. The cut tissue sections were immersed in 100% xylene twice for 10 minutes to dissolve the paraffin, consecutively immersed in 100% ethanol, 90% ethanol, 80% ethanol, and 70% ethanol each for 5 minutes, and then finally rinsed with water. The paraffin-removed tissue slides were subjected to hematoxyrin & eosin (H&E) staining and observed using a microscope.

Figure 3C:
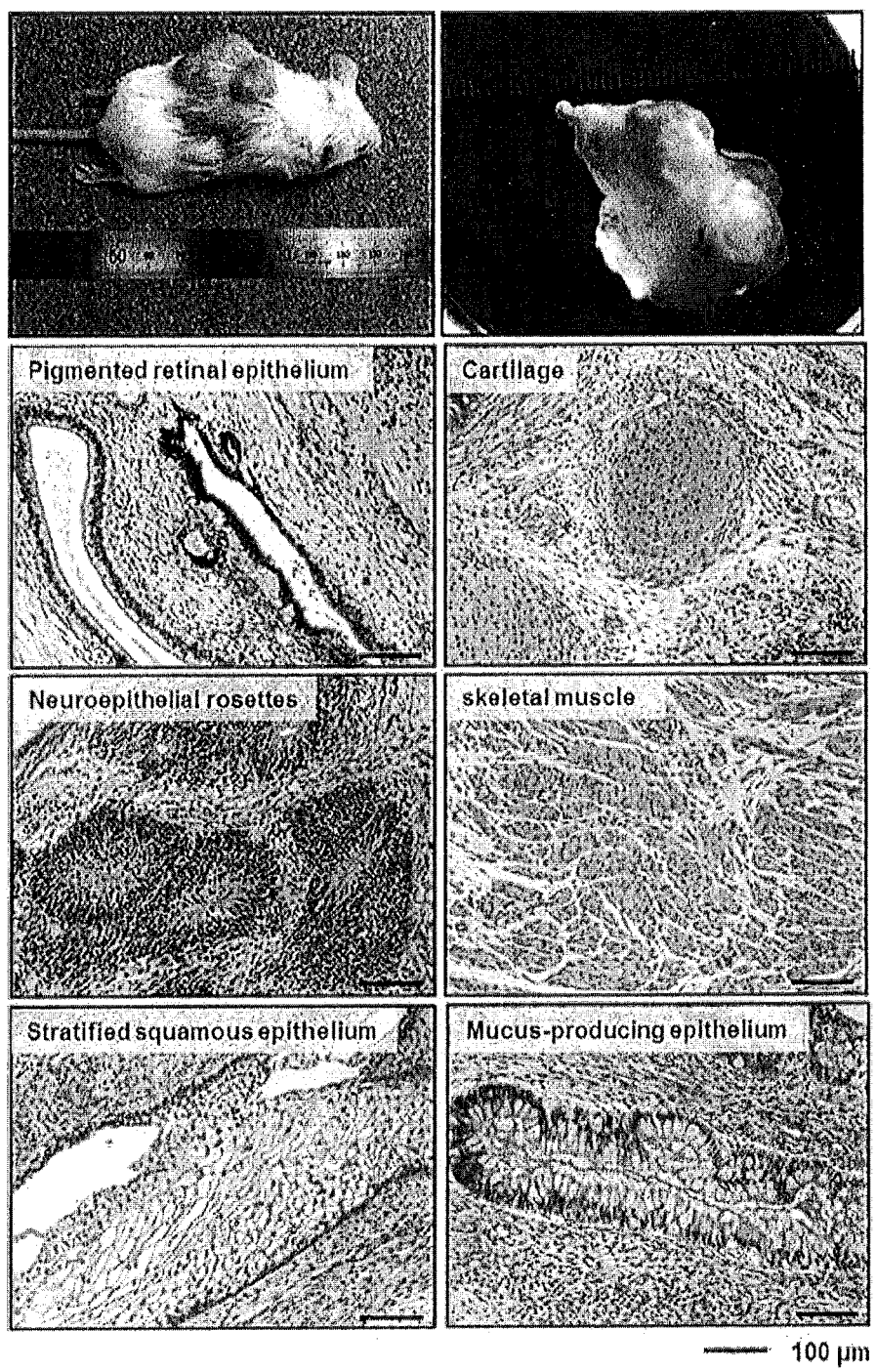
FIG. 3C illustrates verification results of an ability of CiMS-iPSCs to differentiate into three germ layers in vivo through teratoma formation.

As a result, as illustrated in FIG. 3C, various tissues differentiated from the three germ layers were observed through morphological differences.

From the above results, it was confirmed that the CiMS-iPSCs had the ability to differentiate into three germ layers in vitro and in vivo.

Example 5. Comparison of Production Efficiency of CiMS-iPSCs

To compare with the production efficiency of the CiMS-iPSCs prepared using the methods of Examples 1 and 2, a retrovirus expressing green fluorescent protein (GFP) was prepared according to the method of Example 2-1, and then the efficiencies of virus transfection into CiMSs, skin fibroblasts, and 293T cells were compared with one another.

Figure 4A:
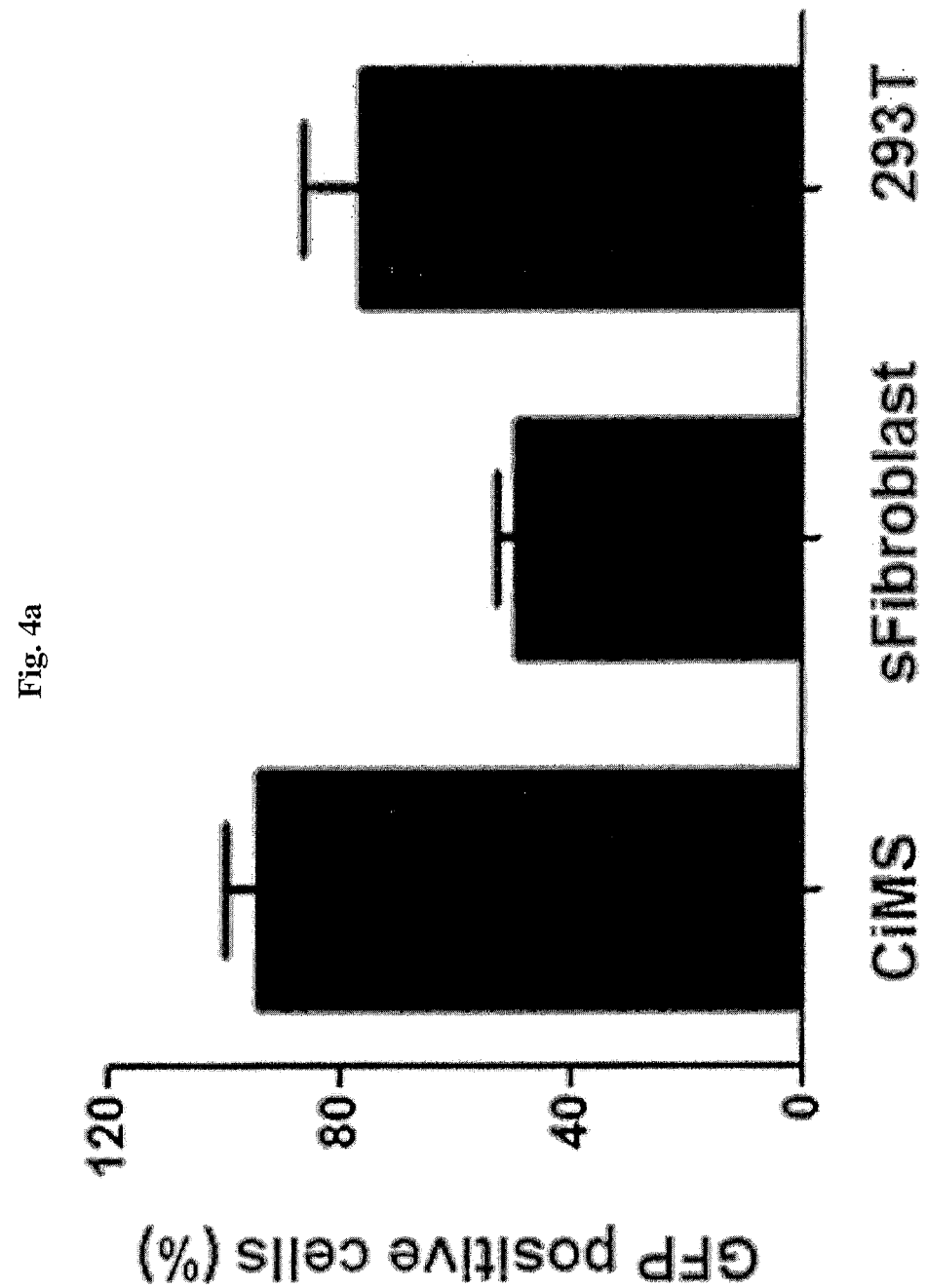
FIG. 4A illustrates results of comparison in efficiency between CiMSs, skin fibroblasts, and 293T cells that were transduced with a GFP-expressing retrovirus.

As a result, the CiMSs exhibited a viral titer of $13.3 \times 10^3$ TU/μl (transduction units/μl), whereas the skin fibroblasts exhibited a viral titer of $8.3 \times 10^3$ TU/μl and the 293T cells, which are known to be easily transfected, exhibited a viral titer of $11.3 \times 10^3$ TU/μl. As illustrated in FIG. 4A, these results led to differences between transfection efficiencies of the GFP-expressing retrovirus (CiMSs: 93.8%, skin fibroblasts: 49.4%, 293T cells: 76.4%).

Figure 4B:
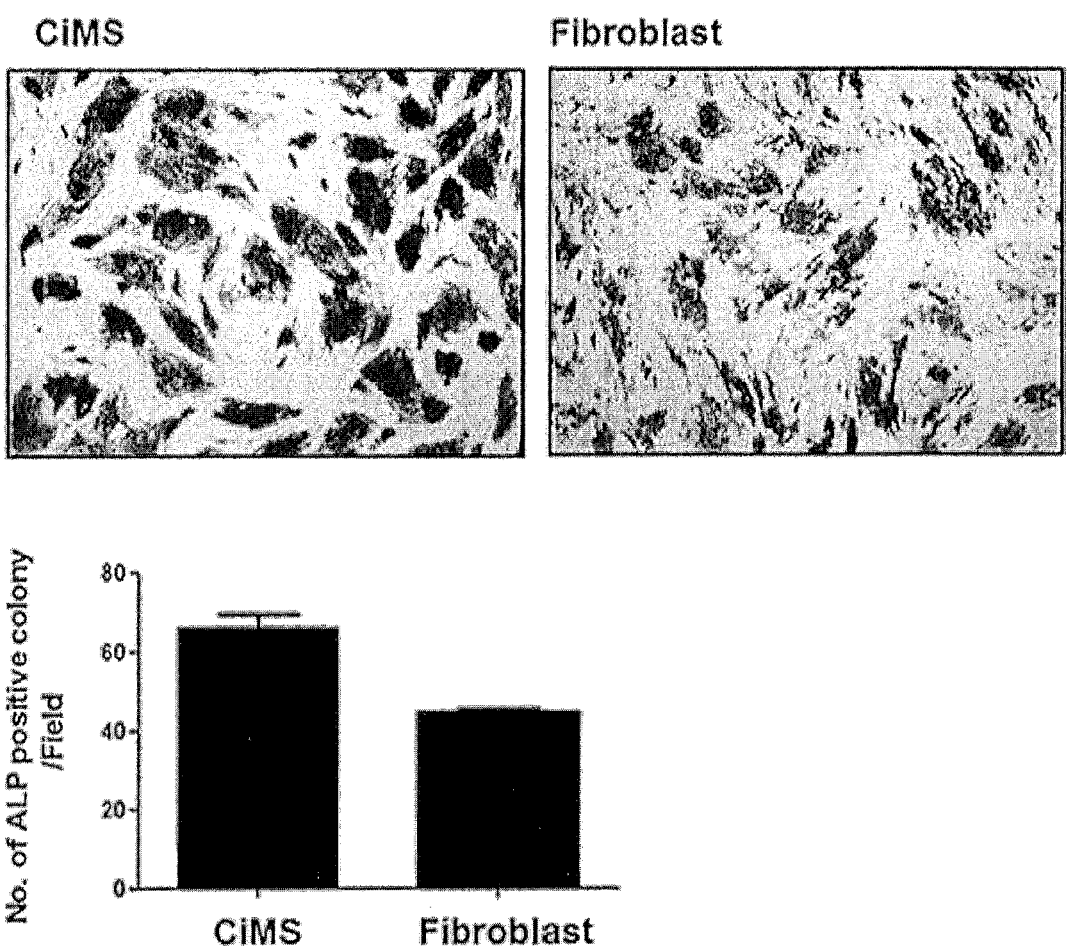
FIG. 4B illustrates results of comparison in iPSC production efficiency between CiMSs and skin fibroblasts that were subjected to alkaline phosphatase (ALP) staining on day 9 after being transduced with Yamanaka factors.

In addition, as illustrated in FIG. 4B, as a result of performing ALP staining on the CiMSs and the skin fibroblasts after being transfected with Yamanaka factors, in the case of CiMSs, an increase of 66% in the formation of ALP positive colonies was exhibited, 1.5 times higher than that in the case of the skin fibroblasts, i.e., 44%. Through the above results, it was confirmed that iPSCs were produced at a 1.5-fold higher efficiency in the case of CiMSs than in the case of the skin fibroblasts, which are primary cells widely used to produce induced pluripotent stem cells using retroviruses expressing Yamanaka factors.

Example 6. Construction of CiMS-iPSC Bank

Figure 5:
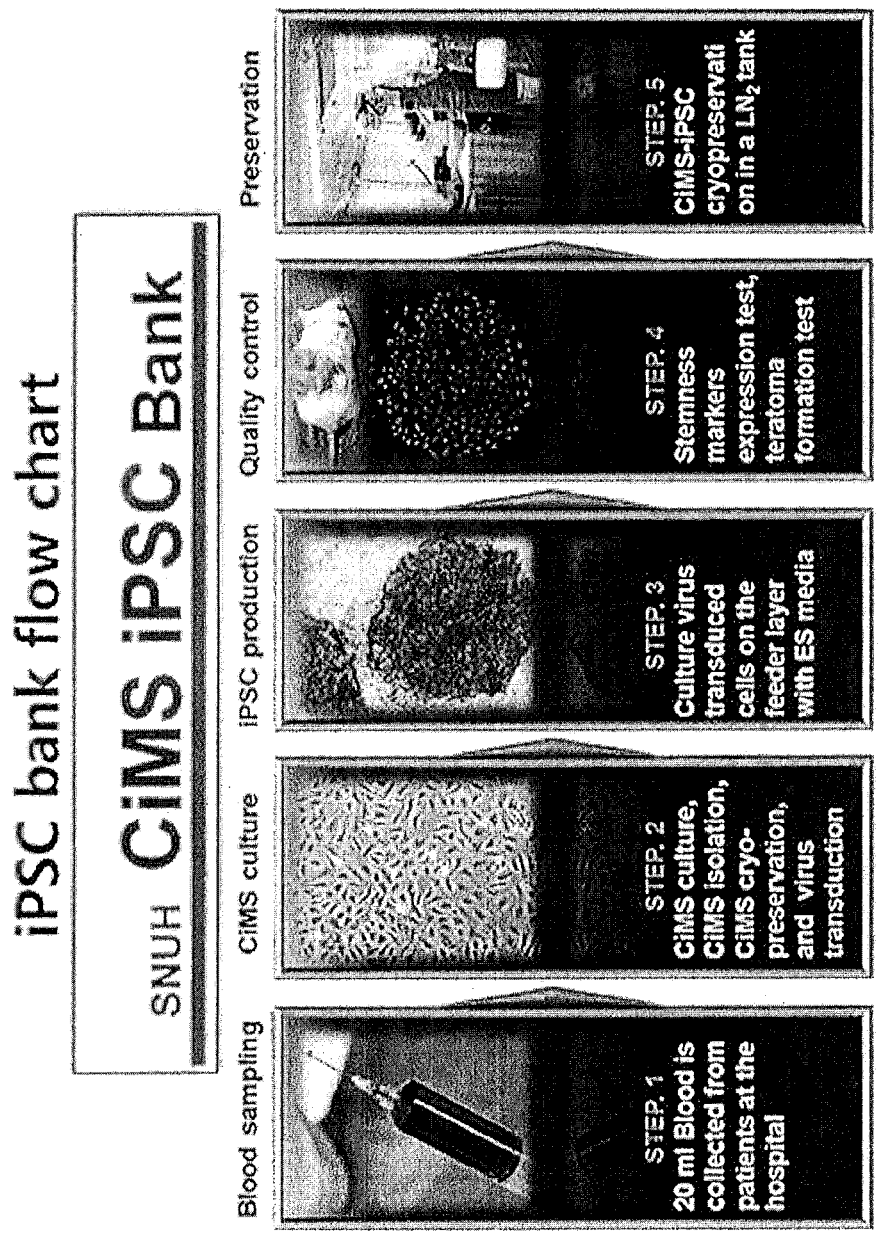
FIG. 5 illustrates a step-by-step process of constructing a CiMS-iPSC bank.

To construct a bank of the CiMS-iPSCs produced according to the methods of Examples 1 and 2, a human-derived iPSC bank was self-constructed through the process illustrated in FIG. 5.

Specifically, CiMS-iPSCs were mainly produced by isolating CiMSs from the blood of healthy volunteers aged between 0 (cord blood) and 77 years old and patients with cardiovascular diseases such as cardiac rhythm, heart transplantation, dysmorphic angina, and the like, and iPSCs of patients with amyotrophic lateral sclerosis (ALS) and Kennedey's syndrome, produced using skin fibroblasts, iPSCs produced from cells obtained from urine, iPSCs produced using dermal papilla cells of patients with alopecia, and the like were also produced and stored to compare with the production efficiency of the CiMS-iPSCs, and about 55 lines of CiMS-iPSCs were constituted.

The ages and gender of volunteers who provided blood did not affect the production efficiency of CiMS-iPSCs. The stored CiMS-iPSCs have many potential applications such as research on the mechanism of cardiovascular diseases, the use thereof for new drug screening by differentiating into patient-customized cells and being used as a disease model, and the like.

Example 7. Differentiation into Cardiovascular Cells Using CiMS-iPSCs

7-1. Differentiation into Mesoendodermal Cells from CiMS-iPSCs

Matrigel was diluted in an ES medium not including a knockout serum replacement and bFGF to a concentration of 1 mg per well of a 6-well plate, and the plate was coated with the diluted Matrigel and put in an incubator at 37° C. for 30 minutes. After 30 minutes, the Matrigel solution was removed and the #1 plate was rinsed once with the same ES medium as described above. Meanwhile, 1 ml of mTeSRTM1(Stem cell Technologies) was mixed with CiMS-iPSCs cut and removed into an appropriate size, 10 µM Y27632, which is a ROCK inhibitor, was added to 1 ml of new mTeSRTM1, followed by mixing with CiMS-iPSCs, and the Matrigel-coated 6-well plate was inoculated with the resulting mixture. The CiMS-iPSCs were cultured for 7 days while replacing the medium with an mTeSRTM1 medium every day under feeder cell-free conditions. On day 7, the mTeSRTM1 medium was removed, the plate was washed twice with PBS, and then 500 µl of a StemPro®Accutase®cell dissociation reagent (Life Technologies) was added to each well and maintained at 37° C. for 5 minutes so that the CiMS-iPSCs became a single cell state. Then, 1 ml of mTeSR1 containing 10 µM Y27632 was added to each well, the cells were completely recovered in a 15-ml tube, the tube was filled with a medium, followed by centrifugation at 300×g for 3 minutes, and then a supernatant was removed. The single cell pellet was lysed in 1 ml of mTeSR1 containing 10 µM Y27632, 10 µl of the solution was taken, and the number of cells therein was measured. Subsequently, $1.5 \times 10^5$ to $2 \times 10^5$ cells/well were inoculated in the Matrigel-previously coated plate.

On the following day, for differentiation into mesoendodermal cells, 10 µM CHIR99021 was diluted in a B27-containing RPMI1640 medium, and the cells were treated with the diluted medium and cultured for 2 days. As a result, it was confirmed that the cells differentiated into Brachyury T expressing cells (Brachyury T positive cells) at an efficiency of 75.51%.

Thereafter, consecutive differentiation of the mesoendodermal cells differentiated at a high efficiency of about 75% through the method, into three conditions: endothelial cells, smooth muscle cells, and cardiomyocytes, was performed. However, since the cells obtained immediately after differentiation was completed have traits of progenitors (pEC, pVSMC, and pCMC), these cells were subjected to a series of processes of maturing, thereby finally obtaining authentic cardiovascular cells (aEC, aVSMC, and aCMC) through differentiation.

Figure 6A:
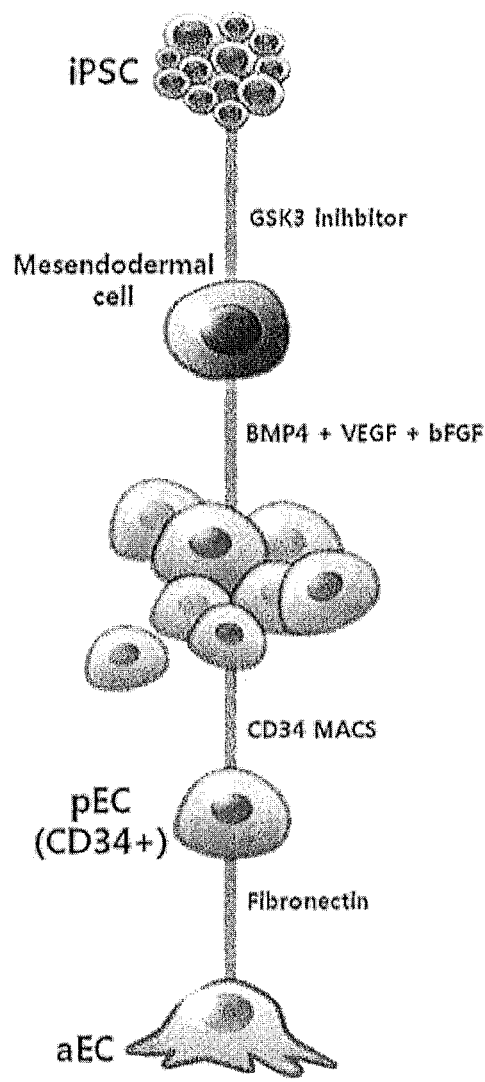
FIG. 6A illustrates a schematic process and protocol of differentiation of CiMS-iPSCs into endothelial cells.
Figure 6A:
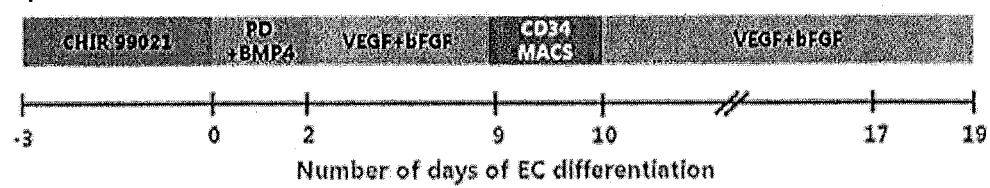

Example 7-2. Verification of Differentiation of CiMS-iPSCs into Endothelial Cells To differentiate the mesoendodermal cells differentiated using the method of Example 7-1 into endothelial cells, the mesoendodermal cells differentiated according to the image and differentiation protocol illustrated in FIG. 6A were treated with 25 ng/ml of BMP4 and 10 µM PD98059, which is an Akt inhibitor, for 2 days so as to differentiate into mesoendodermal cells. Subsequently, the cells were treated with 100 ng/ml of VEGF and 50 ng/ml of bFGF while replacing the medium every day for 7 days to 10 days, and the treatment period was adjusted to increase the number of CD34 expressing cells. Then, CD34 MACS was performed to uniformly acquire only the CD34 expressing cells. Specifically, the supernatant of cells being cultured was removed, and then the cells were washed twice with PBS and treated with 0.05% trypsin-EDTA to remove the cells, and the collected cells were centrifuged at 1,200 rpm for 5 minutes. The cell pellet was lysed in 500 µl of an MACS washing solution containing PBS and 1.0% FBS, and then 50 µl of CD34 MACS antibodies (Military) was added thereto and allowed to react at 4° C. for 30 minutes. After 30 minutes, the cells were centrifuged at 1,200 rpm for 5 minutes and passed through a MACS LS column to obtain only CD34-positive cells. The CD34-positive cells were suspended in an EGM medium supplemented with 100 ng ml of VEGF and 50 ng/ml of bFGF and inoculated in a Matrigel-coated plate to obtain progenitor ECs (pECs). Then, the pECs were sub-cultured while replacing the EGM medium every day to be allowed to differentiate into authentic ECs (aECs). Afterwards, the differentiated cells were compared with human umbilical vein endothelial cells (HUVECs) as a positive control, to verify the function and morphology of endothelial cells.

Figure 6B:
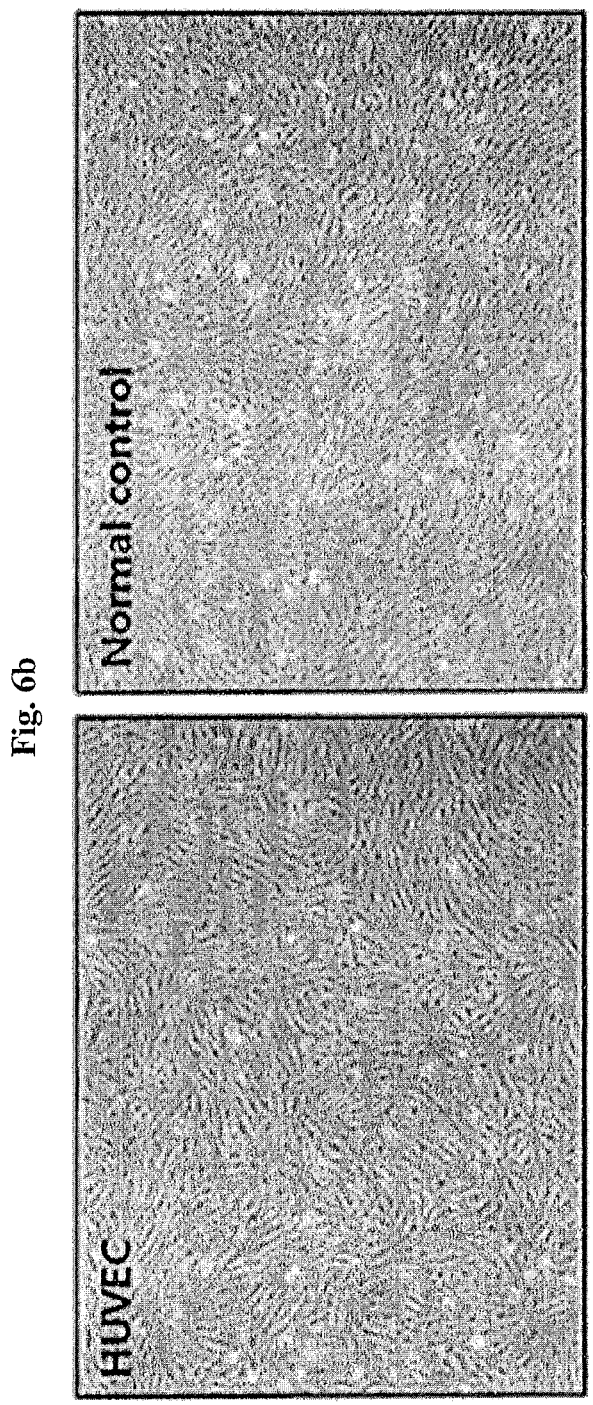
FIG. 6B illustrates microscopic observation results of the comparison between the morphology of endothelial cells obtained by differentiation of CiMS-iPSCs and the morphology of human umbilical vein endothelial cells (HUVECs) as a positive control.
Figure 6C:
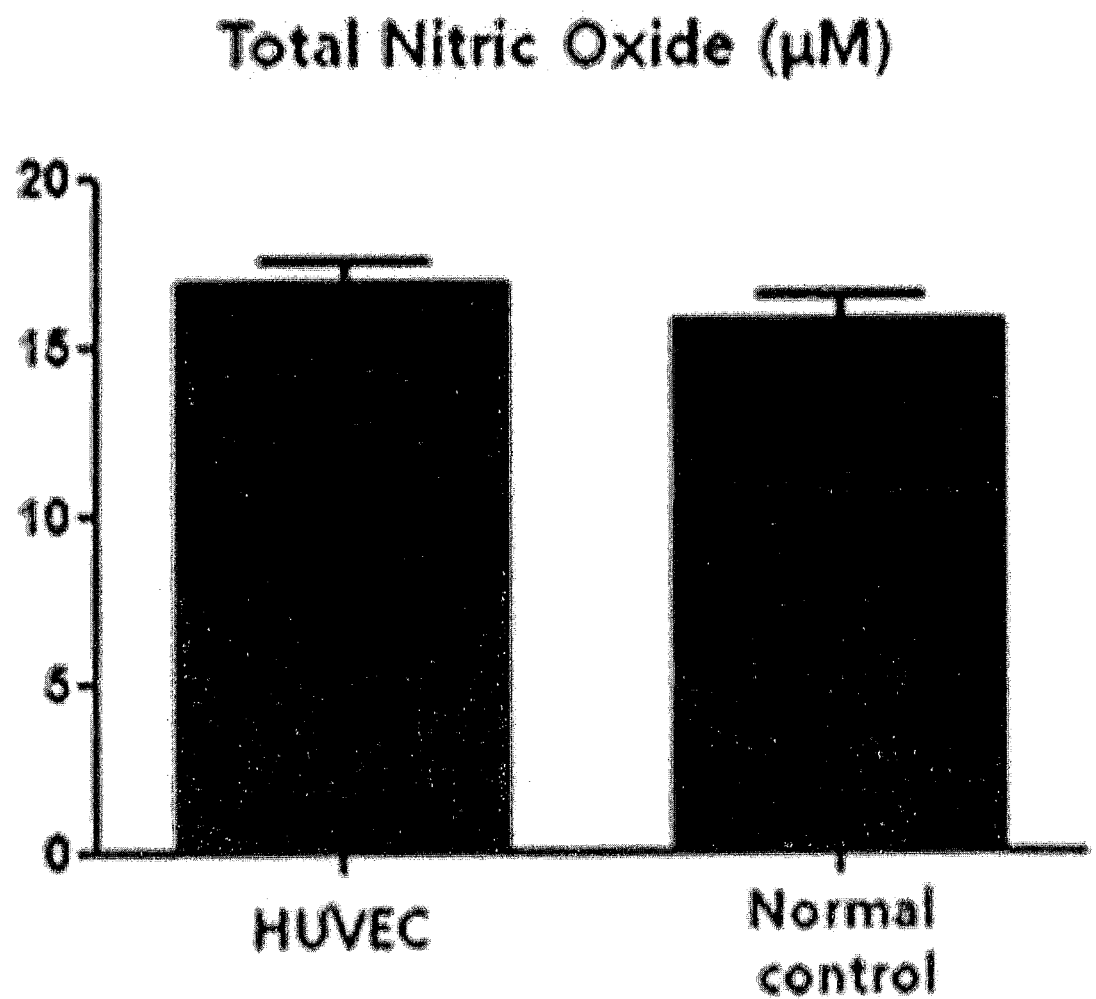
FIG. 6C illustrates measurement results showing a comparison in the concentration of nitric oxide between endothelial cells obtained by differentiation of CiMS-iPSCs and HUVECs as a positive control.

As a result of microscopic observation, as shown in FIG. 6B, the obtained endothelial cells (normal control) were observed to be very similar in morphology to HUVECs, and a total nitric oxide content illustrated in FIG. 6C was found to be almost similar to that of HUVECs. In addition, as illustrated in FIG. 6D, it was observed that endothelial cell expression markers, a platelet-endothelial cell adhesion molecule (PECAM) and VE-Cadherin, were expressed in the endothelial cells obtained by differentiation, and Matrigel tube formation and low density lipoprotein (LDL) uptake were also confirmed.

From the above results, it was seen that differentiation into endothelial cells from CiMS-iPSCs was performed at a high efficiency.

Example 7-3. Verification of Differentiation of CiMS-iPSCs into

Smooth Muscle Cells

Figure 7A:
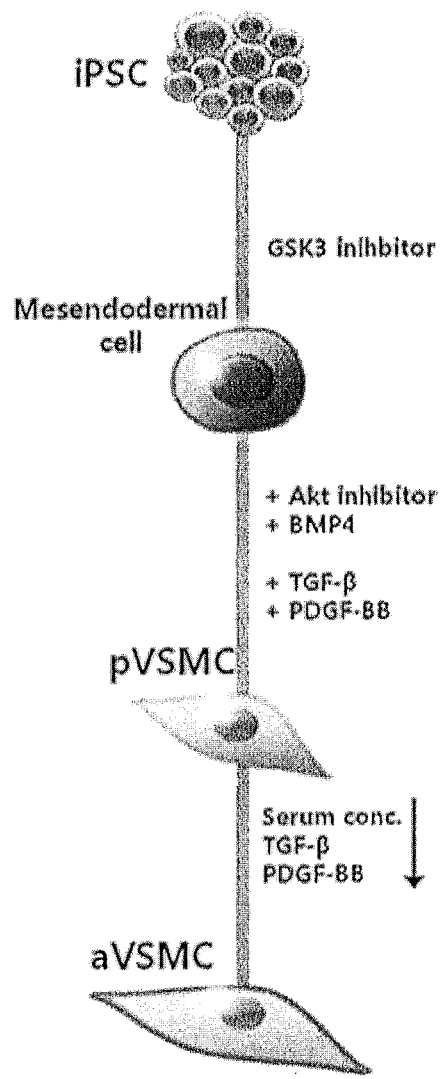
FIG. 7A illustrates a schematic process and protocol of differentiation of CiMS-iPSCs into smooth muscle cells.
Figure 7A:
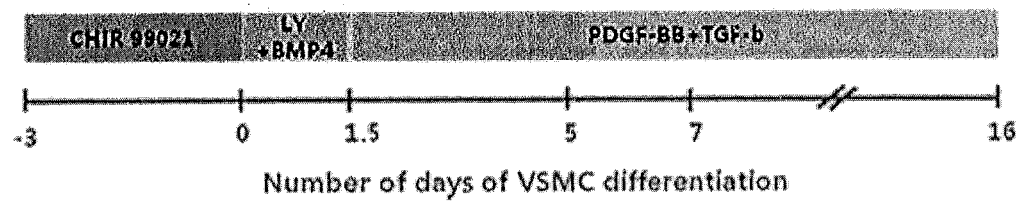

Differentiation into smooth muscle cells was performed using mesoendodermal cells differentiated from CiMS-iPSCs by the method of Example 7-1, in the same manner as the endothelial cell differentiation method of Example 7-2. The mesoendodermal cells were treated with 100 ng/ml of BMP4 and 10 µM LY294002, which is a PI3K inhibitor, according to the illustration and differentiation protocol illustrated in FIG. 7A, and on the following day, 2 ng/ml of TGF-β and 20 ng/ml of PDGF-BB were added to an EGM medium and the cells were cultured in the resulting medium for 14 days. During the culture period, cells appearing early were progenitor VSMCs (pVSMCs) and exhibited a synthetic smooth muscle cell pattern, but the cells grown in Matrigel after further culturing were sub-cultured two to three times in a type II collagen-coated dish to thereby obtain authentic VSMCs (aVSMCs: contractile VSMCs). To verify the obtained VSMCs, these cells were compared with human gastric vascular smooth muscle cells (hVSMCs) as a positive control.

Figure 7B:
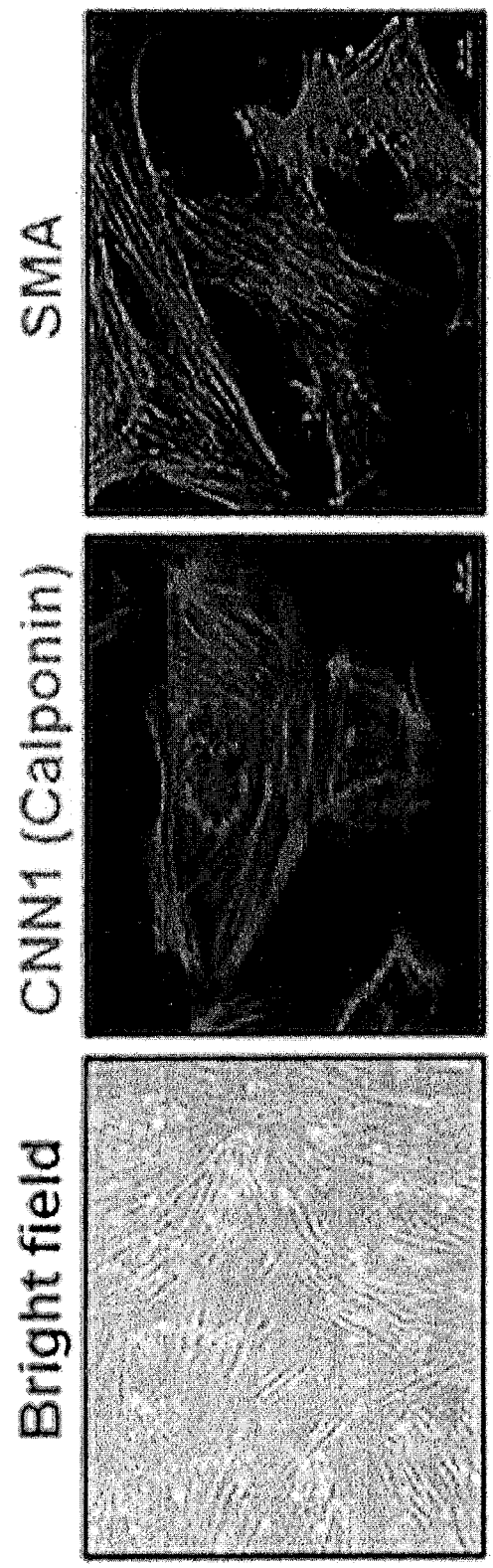
FIG. 7B illustrates verification results of the protein expression of smooth muscle cell markers (Calponin and SMA) through immunofluorescence staining in smooth muscle cells obtained by differentiation from CiMS-iPSCs.
Figure 7C:
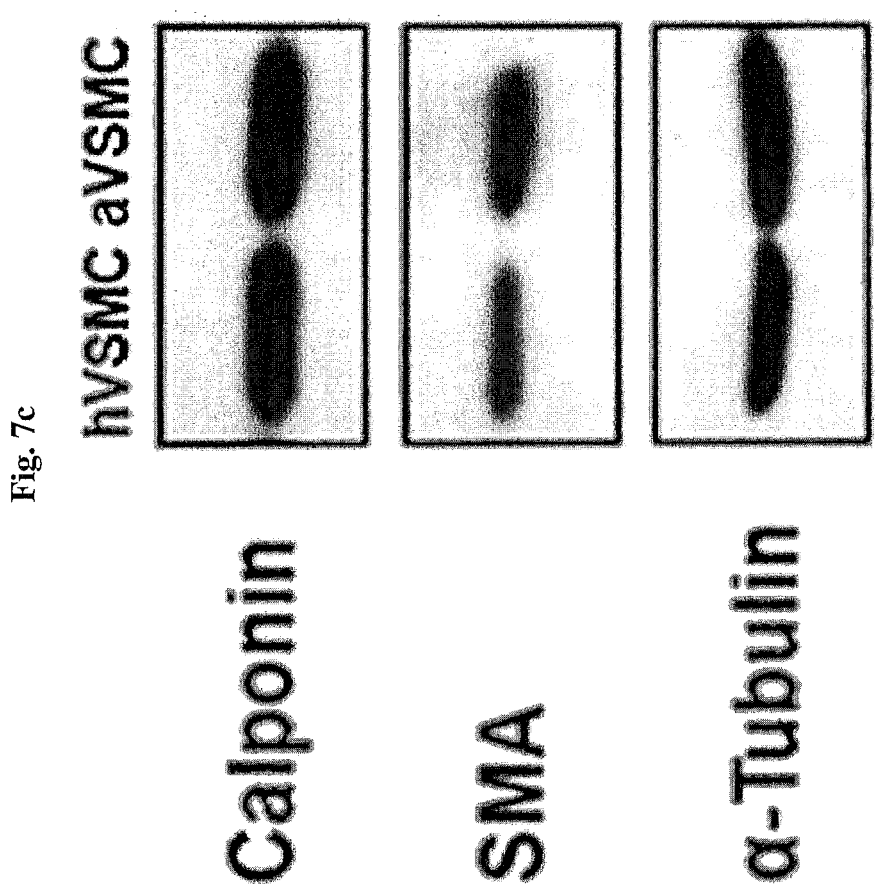
FIG. 7C illustrates results of comparison between protein expression levels of smooth muscle cell markers (Calponin and SMA) through Western blotting in smooth muscle cells differentiated from CiMS-iPSCs and human gastric vascular smooth muscle cells (hVSMCs) as a positive control.
Figure 7D:
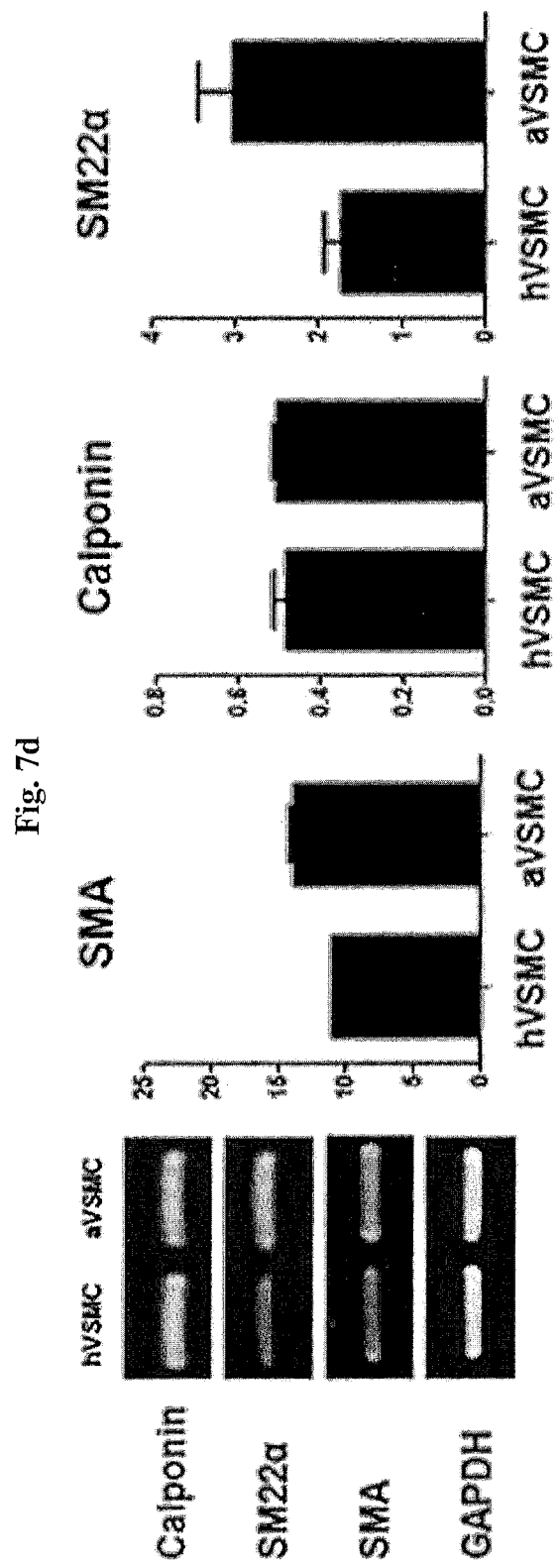
FIG. 7D illustrates results of comparison between mRNA expression levels of smooth muscle cell markers (Calponin, SMA, and SM22α) through RT-PCR in smooth muscle cells differentiated from CiMS-iPSCs and hVSMCs as a positive control.

As a result of observing protein expression amounts of smooth muscle cell marker genes through immunofluorescence staining and Western blotting, as illustrated in FIGS. 7B and 7C, it was confirmed that proteins of the smooth muscle cell marker genes CNN1 (calponin) and SMA were expressed at almost the same levels as those of the positive control (hVSMCs), and it was also confirmed from RT-PCR results of FIG. 7D that mRNA expression amounts of the marker genes CNN1(calponin), SMA, and SM22a were at much higher levels than those of the positive control.

From the above results, it was confirmed that smooth muscle cells was obtained with high efficiency by differentiation from CiMS-iPSCs using the method.

Example 7-4. Verification of Differentiation of CiMS-iPSCs into Cardiomyocytes

Figure 8A:
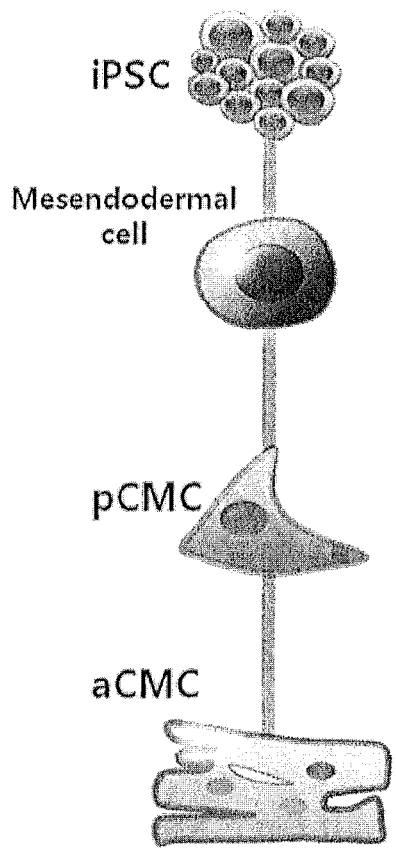
FIG. 8A illustrates a schematic process and protocol of differentiation of CiMS-iPSCs into cardiomyocytes.
Figure 8A:
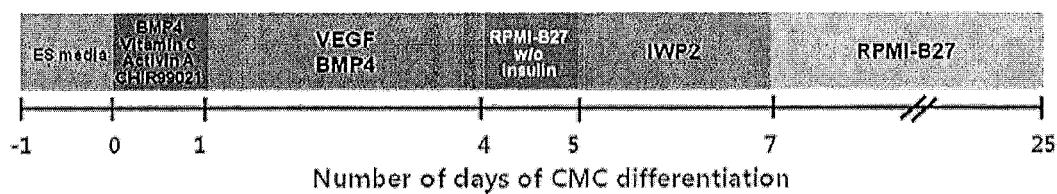

Differentiation into cardiomyocytes was performed according to the protocol illustrated in FIG. 8A in the embryonic body form of CiMS-iPSCs. Specifically, the ES medium of CiMS-iPSCs being cultured was removed, 0.5 mg/ml of dispase was dissolved in a bFGF-free ES medium, the cells were treated with 1 ml of the resulting ES medium and then cultured at 37° C. for 1 hour so that the CiMS-iPSC colonies were separated from feeder cells. The suspended CiMS-iPSC colonies were collected and transferred to a 15-ml tube and the CiMS-iPSCs were washed twice with a bFGF-free ES medium. On the following day, 3 µM CHIR99021, 25 ng/ml of BMP4, 50 µg/ml of vitamin C, and 100 ng/ml of activin A were added to an RPMI1640 medium containing insulin-free B27 (RPMI1640+insulin-free B27), and the CiMS-iPSC colonies were cultured accurately for 24 hours. Then, 10 ng/ml of BMP4 and 10 ng/ml of VEGF which were diluted were added to the RPMI1640+insulin-free B27 medium, followed by further culturing for 3 days, and then the cells were rinsed with the RPMI1640+insulin-free B27 medium, followed by further culturing for 1 day. On the following day, 5 µM IWP2, a low-molecular substance for inhibiting the Wnt signaling pathway, was added to the cells, followed by culturing for 2 days and then continuous culturing in an RPMI1640+B27 medium, thereby obtaining beating cardiomyocytes (CMCs).

Figure 8B:
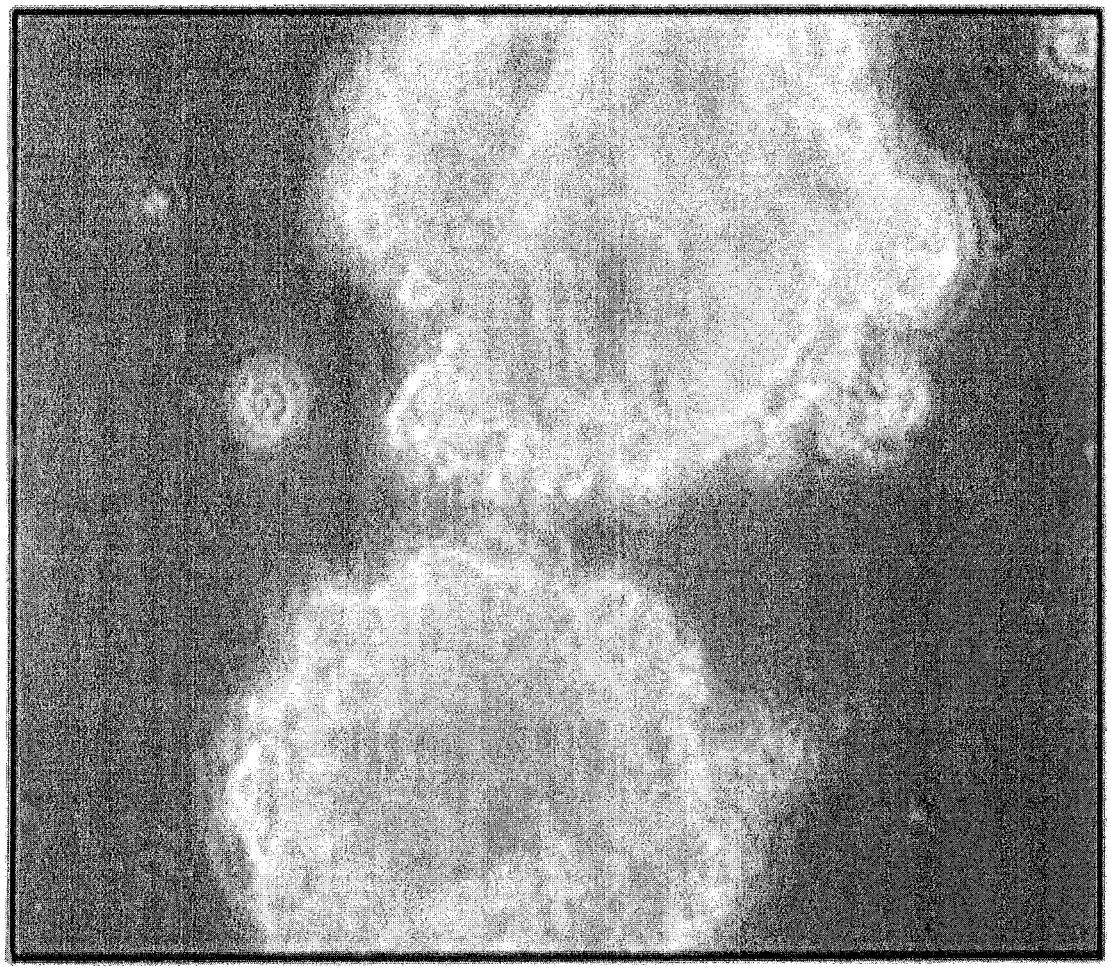
FIG. 8B illustrates a microscopic image of beating embryonic bodies differentiated into cardiomyocytes from CiMS-iPSCs.

As a result of microscopic observation of the cardiomyocytes obtained by the differentiation method, as illustrated in FIG. 8B, beating embryonic bodies were confirmed. From the above results, it was confirmed that differentiation of the CiMS-iPSCs into cardiomyocytes was satisfactorily performed using the method.

The above description of the present invention is provided only for illustrative purposes, and it will be understood by one of ordinary skill in the art to which the present invention pertains that the invention may be embodied in various modified forms without departing from the spirit or essential characteristics thereof. Thus, the embodiments described herein should be considered in an illustrative sense only and not for the purpose of limitation.

The invention claimed is:

1. A method of preparing induced pluripotent stem cells, the method comprising:
   producing endocardium-derived adult stem cells by:
      suspending and seeding peripheral blood mononuclear cells (PBMCs) isolated from peripheral blood in an endothelial cell growth medium (EGM),
      removing T cells, and
      culturing the resulting cells while replacing the medium every day for 5 days to 8 days;
   introducing, into the endocardium-derived adult stem cells, a gender-determining region Y (SRY)-box 2 (SOX2) gene, a v-myc avian myelocytomatosis viral oncogene homolog (c-MYC) gene, an octamer-binding transcription factor 4 (OCT4) gene, and a Kruppel-like factor 4 (KLF4) gene to provide gene-introduced cells;
   producing epithelial-like cells by culturing the gene-introduced cells in an endothelial cell growth medium for 8 days to 12 days while replacing the medium every day;
   mounting the epithelial-like cells on feeder cells and culturing the mounted cells in the endothelial cell growth medium for 3 days to 7 days; and
   subsequently continuing to culture the resulting cells while replacing the endothelial cell growth medium with an embryonic stem cell (ES) medium, which provides induced pluripotent stem cells.

2. The method of claim 1, wherein the feeder cells comprise a mouse-derived embryonic fibroblast cell line.

3. The method of claim 1, wherein the ES medium is Dulbecco's Modified Eagle Medium: Nutrient Mixture F-12 (DMEM/f12) treated with a knockout serum replacement, L-glutamine, non-essential amino acids, 2-mercaptoethanol, penicillin/streptomycin, and bFGF.

* * * * *